US008431170B2

United States Patent
Ahlnäs

(10) Patent No.: US 8,431,170 B2
(45) Date of Patent: Apr. 30, 2013

(54) ANTIMICROBIAL COMPOSITION WITH LOW CYTOTOXICITY

(75) Inventor: Thomas Ahlnäs, Kotka (FI)

(73) Assignee: Oy Granula AB Ltd., Kotka (FI)

( * ) Notice: Subject to any disclaimer, the term of this patent is extended or adjusted under 35 U.S.C. 154(b) by 407 days.

(21) Appl. No.: 12/626,072

(22) Filed: Nov. 25, 2009

(65) Prior Publication Data

US 2010/0129302 A1    May 27, 2010

Related U.S. Application Data

(60) Provisional application No. 61/117,684, filed on Nov. 25, 2008.

(51) Int. Cl.
A61K 36/00 (2006.01)
A61K 38/00 (2006.01)
C07C 291/00 (2006.01)

(52) U.S. Cl.
USPC ........... 424/779; 424/725; 534/571; 514/10.2

(58) Field of Classification Search ................ 424/779, 424/725; 534/571; 514/10.2
See application file for complete search history.

(56) References Cited

U.S. PATENT DOCUMENTS

| | | | | |
|---|---|---|---|---|
| 6,835,374 B2 * | 12/2004 | Parekh et al. | ................ | 424/65 |
| 2005/0169947 A1 * | 8/2005 | Korte et al. | ................... | 424/401 |
| 2006/0257347 A1 * | 11/2006 | Kim et al. | ................. | 424/70.13 |
| 2007/0166255 A1 * | 7/2007 | Gupta | ........................ | 424/70.1 |

FOREIGN PATENT DOCUMENTS

| WO | WO 2004/000304 A1 | | 12/2003 |
|---|---|---|---|
| WO | WO 2005/047423 | * | 5/2005 |
| WO | WO 2005/047423 A1 | | 5/2005 |
| WO | WO 2007/096088 A1 | | 8/2007 |
| WO | WO 2007/096089 A1 | | 8/2007 |
| WO | WO 2007/096090 A1 | | 8/2007 |
| WO | WO 2008/020112 A1 | | 2/2008 |

OTHER PUBLICATIONS

Hearon et al. Conidendrin I. Its Isomerization and Demethylation; J. Am. Chem. Soc, 1951 (73) pp. 4005-4007.*
Swidinsky et al. The Preparation of Some Nitrogenous Derivatives of Conidendrin; J. Am. Chem. Soc. 1953 (76) pp. 1148-1159.*
Anna-Liisa Valimaa et al., "Antimicrobial and cytotoxic knotwood extracts and related pure compounds and their effects on food-associated microorganisms", International Journal of Food Microbiology, 2007, pp. 235-243, vol. 115, Elsevier.
Bjarne Holmhbom et al., "Knots in trees—A new rich source of lignans", Phytochemistry Reviews, 2003, pp. 331-340, vol. 2.

* cited by examiner

*Primary Examiner* — Patricia Leith
(74) *Attorney, Agent, or Firm* — Young & Thompson

(57) ABSTRACT

A composition having antimicrobial activity is provided. The composition includes a compound mixture obtained from pulverized and/or extracted wood material that contains polyphenols (i) lignans, (ii) stilbenes and (iii) oligomers of lignans, stilbenes juvabiones or flavonoids. The cytotoxicity of the polyphenols in the compound mixture is at least ten times lower compared to butylated hydroxytoluene (BHT) and does not irritate the skin in a so-called single patch test at 0.1 wt %. The composition further includes an antimicrobial agent such as betulin, betulonic acid, betulinic acid, betuloinic acid, resveratrol or ethylhexyl glyceryl. The composition can be used in cosmetic and hair care products.

12 Claims, No Drawings

ANTIMICROBIAL COMPOSITION WITH LOW CYTOTOXICITY

RELATED APPLICATIONS

This application is based on provisional application No. 61/117,684 filed on 25 Nov. 2008.

TECHNICAL FIELD

The invention relates to compositions with low cytotoxicity and inhibiting the growth of micro-organisms. The compositions may be used in a cosmetic composition, food industry composition, animal feed composition, for producing a technical composition or a packing material composition.

BACKGROUND

In cosmetic and food industry compositions, in commercial solvents and detergents as well as in industrially employed solvents, it is often necessary to add antimicrobial agents, such as agents inhibiting the growth of microbes, and microbicidic agents. Antimicrobial agents may themselves be cytotoxic, skin irritative or otherwise harmful to the system when getting into contact with the skin. Moreover, the currently used antimicrobial agents are without exception synthetic, which means that their production is a complicated process.

OBJECT OF THE INVENTION

The object of the invention is to eliminate the above described drawbacks of the prior art.

Thus, the principal object of the invention is to realize such compositions or semi-finished compositions used in the production of said compositions, where the antimicrobial agent contained by the compositions or their semi-finished composition is obtained from the nature, and where the undesirable properties are minimal. Undesirable properties are for example cytotoxicity, other physiological toxicity, skin irritation and tendency to form or induce free radicals on the skin, for instance as the substance is decomposed owing to the effect of sunlight. For instance phenoxyethanol (derivative of benzoic acid) is a relatively wide-scale synthetic microbicide and preservative, used generally in foodstuffs and cosmetic compositions, because it is effective against both yeasts, fungi and Gram-negative bacteria. However, its use is restricted, because it has been found to be physiologically toxic, allergenic and skin irritative, in addition to which it decomposes owing in sunlight, thus forming free radicals. The object of the invention is to reduce the use of generally used synthetic substances inhibiting microbial growth on a wide scale, or to completely replace said substances, particularly in cosmetic compositions and food industry compositions, by a corresponding substance obtained from natural sources, which substance causes minimal irritation to mammal skin and has a minimal cytotoxicity.

Here the term 'substances inhibiting microbial growth on a wide scale' particularly refers to a substance that inhibits the growth of both Gram-positive bacteria and Gram-negative bacteria as well as yeasts and fungi. At least wide scale microbial growth inhibition refer to inhibition of growth at Gram-negative bacteria of E. coli, Ps. aeruginosa, Ps. putida, Kl. pneimoniae; from among Gram-positive bacteria at least the growth of S. aureus; from among yeasts at least the growth of M. furfur and C. albicans; and from among fungi at least the growth of A. niger.

A further object of the invention is to reduce the harmful properties of another substance inhibiting microbial growth contained in a composition, such as a synthetic substance inhibiting microbial growth on a narrow scale, by a compound mixture with a good availability and low production expenses. One of the most significant harmful properties is the cytotoxicity of a substance inhibiting microbial growth on a narrow scale.

Yet another object of the invention is to realize cosmetic industry compositions or food industry compositions or semi-finished compositions used for manufacturing these compositions, which composition or semi-finished composition contains as few antimicrobial agents as possible.

GENERAL DESCRIPTION OF THE INVENTION

The invention concerns a composition comprising a compound mixture, which has been obtained by pulverizing wood material and/or by extracting wood material, so that said compound mixture contains at least two different compounds selected from the group consisting of: lignans, stilbenes, juvabiones, flavonoids, betulin, betulonic acid, betulinic acid, betuloinic acid, and ester derivatives, ether derivatives or stereoisomers of said compounds, said compound mixture containing also oligomers of said compounds, providing that the compound mixture contains lignans 50-99.9 wt %,
oligomers of lignans, stilbenes, juvabiones or flavonoids 1-31 wt %, and
at least one compound selected from the group consisting of: 7-hydroxymatairesinol, conidendrin, conidendric acid, alpha-conidendrin, alpha-conidendric acid, isohydroxymatairesinol, cyclolariciresinol, secoisolariciresinol, anhydrosecoisolariciresinol, stilbenes, and ester derivatives, ether derivatives or stereoisomers of said compounds. The composition may further comprise a carrier agent. The composition may be used in a product.

Especially, the invention relates to a method for producing a cosmetic composition, food industry composition, animal feed composition, technical composition or packing material composition, said composition containing a widely antimicrobialally effective agent, a carrier agent such as solvent, with either hydrophobic or hydrophilic nature, selected according to the target of usage, as well as a possible surface active agent. Hence:

in the composition, there is included carrier agent, possible auxiliary agents and possible surface active agent conventionally used in a cosmetic composition, food industry composition, animal feed composition, technical composition or packing material composition, in the composition, there is included a compound mixture with an antimicrobial effect on a wide scale, which is obtained by pulverizing wood material from one or preferably two different wood species and/or by extracting the possibly pulverized wood material from two different wood species, so that said compound mixture contains at least two different compounds selected from among the following group: lignans according to general formulas IA and IB (Appendix), stilbenes according to general formula II (Appendix), juvabiones according to general formula III (Appendix), flavonoids according to general formula IV (Appendix) and betulin and its derivatives (betulinic acid, betuloinic acid or betulonic acid), said compound mixture also containing oligomers of said polyphenolic compounds providing, however, that the compound mixture contains lignans, particularly 7-hydroxymatairesinol or secoisolariciresinol roughly 50-99.9 wt %; stilbenes, particularly pinosylvin or its ester or ether derivatives roughly 0-70 wt %; oligomers of lignans, or stilbenes or juvabiones or flavonoids roughly 1-31 wt %; providing, however, that the compound mixture contains at least one compound, selected from among the following group: 7-hydroxymatairesinol, secoisolariciresinol, cycloisolariciresinol, anhydrosecoisolariciresinol, α-conidendrin, α-conidendric acid, isohydroxymatairesinol and stilbenes according to formula II, as well as their ether and ester derivatives and stereoisomers. In the composition, there is included said compound mixture 0.1-5 wt % of the total weight of said composition, providing, however, that with said content, the cytotoxicity of said compound mixture dissolved in ethanol with a HaCat cell culture after 24 incubations is lower than the cytotoxicity of 0.02-0.1 wt % BHT dissolved in ethanol in the same incubation conditions, preferably lower than the cytotoxicity of 0.01-0.05 wt % BHT dissolved in ethanol in the same incubation conditions, in addition to which the compound mixture within said content range has wide-scale antimicrobial effects against Gram– bacteria, Gram+ bacteria, yeast and fungi in the composition.

Advantageously the compound mixture is obtained from two different wood species, such as pine and spruce species and contains 7-hydroxymatairesinol or secoisolariciresinol 50-99.9 wt %, stilbene, particularly pinosylvin 0.1-70 wt %, conidendrin 3-6 wt %, lariciresinol 4-7 wt %, liovile 2-5 wt %, or ester or ether derivatives of said stilbene or lignan compounds or their stereoisomers, and also oligomers of lignans, stilbenes, juvabiones or flavonoids 5-8 wt %. However, owing to the relatively high cytotoxicity of stilbenes, a mixed compound mixture of polyphenolic compounds obtained from both pine species and spruce species preferably contains pinosylvins roughly 0.1-20 wt %, if it is added in a foodstuff composition or cosmetic composition. Now the content of stilbenes or their ester or ether derivatives in the end product is roughly if 0.1 wt % at most, in case in the composition there is added 5 wt % mixed extract obtained from two different wood species, said mixed extract containing 10 wt % mixture of phenolic compounds.

Here the term stereoisomers refers to compound diastereomers and to mixtures of different diastereomers, to pure enantiomers and rasemic mixtures of enantiomers.

The invention is first of all based on the surprising discovery that when in a composition meant for a mammal or a composition that in general gets into skin contact with a mammal at some stage, the employed antimicrobial effective agent is a compound mixture of phenolic compounds obtained from extracting and/or pulverizing natural wood material, which mixture is not essentially refined, said compound mixture has remarkably less harmful properties than the generally used wide-scale synthetic antimicrobial agents currently used in compositions, such as previously mentioned phenoxyethanol. The phenolic compound mixture according to the invention does not cause skin irritation even with high contents, is physiologically well tolerated and has a low cytotoxicity.

Secondly, the invention is based on the surprising observation that sufficient attention has previously not been paid to the level of overall cytotoxicity of the effective agents in cosmetic materials, foodstuffs, animal feed and packing materials, but each effective agent to be included in the composition, such as antimicrobial agent, has been added to an extent which its maximum cytotoxicity by any means has allowed. With this observation in mind, the applicant has attempted to achieve compositions where the overall cytotoxicity of the different components of the effective agent is brought as low as possible, while the effect of the effective agent remains the same.

In the present invention, the optimizing of the overall cytotoxicity is realized by using, instead of, or in addition to, the first agent inhibiting the growth of micro-organisms contained in the composition, a compound mixture that is obtained by extracting and/or pulverizing and that is not essentially refined. The mutual ratio between the phenolic compounds contained by said compound mixture, as well as the compounds contained by the compound mixture, can change depending on the effects required in the target of usage. The mutual content of the compounds contained in the compound mixture, the compounds and the effect of the compound mixture, as well as its profile of influence are adjusted depending on the target of usage of the composition, so that by using the compound mixture, there can be achieved a desired antimicrobial effect, while the overall cytotoxicity of the compound mixture is as low as possible and remains within certain limits in comparison with the cytotoxicity of BHT. Compound mixture using can possible second inhibiting the growth of micro-organisms agent harmful properties such as its own cytotoxicity, reduced remarkably target of usage, such as on the skin or hairs of a mammal, for instance by reducing the quantity of the first agent inhibiting the growth of micro-organisms from the conventionally applied level.

The composition can be a cosmetic composition, a food industry composition, an animal feed composition, a technical composition, or a packing material.

The term 'cosmetic composition' here refers to compositions meant for the treatment of the skin, teeth, hair and body hair of mammals. In these, the carrier agent is semisolid material such as cream, gel or paste; solid material such as solid foam; heterogeneous material such as solid matter mixture; liquid material such as homogeneous solution or colloidal solution, such as dispersion or suspension, microemulsion, nanoemulsion, or a gaseous material such as aerosol or mist.

Food industry compositions here refer to both individual foodstuffs and foodstuff products. In this sense, food industry compositions are for example fruits, vegetables etc. individual foodstuffs, but also food industry products and semi-finished products, in the preservation of which there are needed antimicrobial agents.

The packing material composition is a composition where the carrier agent is a packing material that is impregnated by a compound mixture according to the invention, in which there is spread the compound mixture according to the invention.

The carrier in a technical composition is a solvent used in cleaning, a cleaning device such as a cleaning cloth, solid material such as a powder used as a surface treatment agent; or the carrier agent is a solution meant for cleaning the body of a mammal. In the carrier, there is impregnated or otherwise included in the compound mixture according to the invention.

The manufacturing of a compound mixture containing phenolic compounds is simple, and the compound mixture is amply available from wood industry pulping processes, so that the replacing of the effective agent by said compound mixture also is economically beneficial. The compound mixture according to the invention also has several other advantageous properties that its individual components do not necessarily have, so that by using the compound mixture, new properties can be obtained in the manufactured compositions, or that the profile of influence of the antimicrobial agent can be adjusted.

By means with the compound mixture according to the invention, there also is achieved the advantage that by using said compound mixture, antioxidative and free radical capturing properties can be obtained in cosmetic or food industry compositions, so that these types of compounds do not need to be separately added in said compositions.

The compound mixture is advantageously an unrefined powder ground of wood material, or a compound mixture extracted from wood material in an extraction solution, said compound mixture forming a homogeneous solution, suspension or dispersion with the extraction solution. Even more preferably, the compound mixture is an unrefined lignan mixture and/or stilbene mixture placed in a liquid, said compound mixture containing at least two different lignan and/or stilbene compounds. The compound mixture is advantageously obtained by extracting wood material from two different wood species in an alcohol-based solution. Preferably the wood material is obtained from wood knot material or stemwood material from adjacent to knots.

Here the term unrefined compound mixture, raw extract, refers to a compound mixture that is obtained by pulverizing and/or extracting wood or plant material, which mixture has thereafter not been subjected to any such chemical or physical cleaning operations by which one of the compounds of said compound mixture would be completely removed from the compound mixture.

Typical cleaning operations in this sense are chromatography or crystallization of certain compounds from the solution. Instead, the compound mixture may be subjected to such chemical treatments by which the content of one of the compound mixture compounds is adjusted in relation to other compounds contained in the compound mixture. This kind of operation is for example extraction by which the mutual contents of the compounds contained in the solution are adjusted with respect to each other, but by which the compounds are not completely removed. The phenolic compounds contained in the compound mixture may also be transformed into simple derivatives such as their esters, or into completely other stilbene/lignan/flavonoid compounds, for example when the pH of the extract solution is changed.

The compound mixture of phenolic compounds to be included in the composition according to the invention, which compound mixture has free radical capturing properties, contains preferably at least two different compounds selected from the following groups belonging to flavonoids, lignans, juvabiones, stilbenes or betulin or its derivatives:

Lignans:
matairesinol, hydroxymatairesinol, oxomatairesinol, didemethyl matairesinol, didemethyl matairesinol, iso-hydroxymatairesinol, epi-isohydroxymatairesinol and their stereoisomers, among which particularly let us point out hydroxymatairesinol stereoisomers 7S, 8R, 8'R-hydroxymatairesinol and 7R, 8R, 8'R-allohydroxymatairesinol, and their stereoisomers and ester or ether derivatives,
secoisolariciresinol, isolariciresinol, lariciresinol, pinoresinol, dimethyl secoisolariciresinol, 7-hydroxysecoisolariciresinol, cyclolariciresinol, cycloisolariciresinol and their stereoisomers as well as their ester or ether derivatives,
nortrachelogenin and its stereoisomers and ester or ether derivatives,
enterolactone and its stereoisomers and ester or ether derivatives,
conidendrin, α-conidendrin and their stereoisomers as well as ester or ether derivatives,
lignan A and its stereoisomers and ester or ether derivatives,
liovile and its stereoisomers and ester or ether derivatives;

Juvabiones:
juvabiones and their stereoisomers and ester or ether derivatives;

Stilbenes:
pinosylvin, dihydropinosylvin, pinosylvin monomethyl ether, dihydropinosylvin monomethyl ether, resveratrol, astringin, isorhapontine, and their stereoisomers and ester or ether derivatives;

Flavonoids:
pinosembrin, catechin, pinobanxin, kaempferol, dihydrokaempferol, taxifolin, naringenin, teracasidine, ketoteracasidine, isoteracasidine, melacasidine, isomelacasidine and their stereoisomers and ester or ether derivatives,
betulin, betulinic acid, betuloinic acid or betulonic acid and their stereoisomers and esterized forms,
as well as the glycosidized forms of these compound, and their oligomers such as trimers and tetramers. These oligomers are here called oligolignans in case they are oligomers of lignans, stilbenes or juvabiones; free lignans and stilbenes are dimers, having 2 phenylpropane units coupled together by beta-beta bonds, and their oligolignans have 3-6 phenyl propane units ($C_6C_3$) coupled together by beta-beta bonds.

In this connection let us point out that compounds called lignans are generally (poly)phenolic compounds obtained from wood and plants, having 2 phenyl propane units coupled together by beta-beta bonds (IUPAC, 2000), but in this application it has been considered necessary to distinguish lignans, stilbenes and juvabiones from each other owing to their different microbiological effects.

Lignans proper here refers to compounds according to the general formula IA and IB (Appendix).

Now, in formula IA:
R1 or R2 denote, irrespective of each other, residue selected from the groups hydrogen, OH or =O,
or either one of the residues R1 or R2 denotes the oxygen atom —O— bound to carbons 9 and 9', and now forms with carbons 8, 8', 9, 9' a 5-membered oxygenous heterocyclic ring C,
R3 denotes hydrogen or residue selected from the group OH, =O, or it forms a bond to the carbon 6, so that the carbons 6, 1, 7, 8, 8', 7' form a cyclohexane ring that is condensed with the phenyl ring A, and possibly also a ring with C,
R4 denotes hydrogen or methyl,
R5 denotes hydrogen or residue selected from the groups OH and $OCH_3$,
R6 denotes hydrogen or hydroxy,
R7 and R8 denote, irrespective of each other, hydrogen or residue selected from the groups OH and $OCH_3$.

Advantageous lignans according to formula 1A are:
7-hydroxymatairesinol (R1 denotes group =O, R2 denotes the oxygen atom pertaining to the hetero ring C, R4=$CH_3$, R7=$OCH_3$, R3=R5=R8=OH, R6=H, R9=H),
matairesinol (R1 denotes group =O, R2 denotes the oxygen atom pertaining to the hetero ring C, R3=R6=R9=H; R4=$CH_3$, R7=$OCH_3$, R5=R8=OH),
oxomatairesinol, which differs from hydroxymatairesinol in that R3 denotes group =O,
didemethyl matairesinol, which differs from hydroxymatairesinol in that R4 and R3 denote hydrogen,
isohydroxymatairesinol, alpha-conidendrin (R1 denotes group =O, R2 denotes the oxygen atom pertaining to the hetero ring C, R4=CH$_3$, R7=OCH$_3$, R8=OH, R6=H, R3 is a bond to the carbon 6, R9=H), alpha-conidendric acid (R4=CH$_3$, R7=OCH$_3$, R5=R8=OH, R6 denotes group =O, R1=R2=OH, R3 is a bond to the carbon 6, so that the carbons 6, 1, 7, 8, 8',7' form a cyclohexane ring D that is condensed with the phenyl ring A, R9=H), liovile (R4=CH$_3$, R7=OCH$_3$, R3=R5=R6=R8=OH, R1=H, R2 denotes the oxygen atom pertaining to the hetero ring C, R3 denotes a bond to the carbon 6, R9=H), secoisolariciresinol (R1=R2=OH, R3=H, R4=CH$_3$, R7=OCH$_3$, R5=R8=OH, R6=R9=H), dimethyl secoisolariciresinol, which differs from secoisolariciresinol in that R5 and R8 are methoxies, isolariciresinol (R1=R2=OH, R4=CH$_3$, R7=OCH$_3$, R5=R8=OH, R6=H, R3 is a bond to the carbon 6, so that the carbons 6, 1, 7, 8, 8',7' form a cyclohexane ring D, which is condensed with the phenyl ring A, R9=H), cyclolariciresinol (R1=R2=OH, R3= a bond to the carbon 6, so that the carbons 6, 1, 7, 8, 8', 7' form a cyclohexane ring D, which is condensed with the phenyl ring A, H, R4=CH$_3$, R7=OCH$_3$, R5=R8=OH, R6=R9=H), nortrachelogenin (R1 denotes group =O, R2 denotes the oxygen atom pertaining to the hetero ring C, R3=R6=H, R4=CH$_3$, R7=OCH$_3$, R5=R8=OH, R9=OH), In Formula IB:

R10 denotes hydrogen or hydroxy

R11 denotes hydroxy or oxygen, which is bound by a bond to the carbons 7 and 9', forming now an oxygenous non-aromatic 5-membered heterocyclic ring (tetrahydrofuran) F with the carbons 7, 8, 8', 9', which ring is condensed in the hetero ring E (tetrahydrofuran) at the carbons 8, 8', R12 denotes hydrogen or methyl, R13 denotes hydrogen or methoxy, R14 denotes hydrogen or methoxy, R30 denotes hydrogen or group =O.

Advantageous compounds according to formula IB are:

pinoresinol (R13=R14=R12=R10=R30=H, and R11 is oxygen in the hetero ring F), isohydroxymatairesinol (R12=R13=R14=R10=H, R11=OH, R30 denotes group =O), lariciresinol (R12=R13=R14=R10=R30=H, R11=OH), and lignan A (R10=R11=OH, R12=R13=R14=R30=H).

Stilbenes in turn refer to compounds according to the general formula II (Appendix), where R15 denotes hydrogen or hydroxy R16 denotes residue selected from the groups H, OH, OCH$_3$, R17 denotes residue selected from the groups OH or OCH$_3$, R18 and R19 denote, irrespective of each other, hydrogen or hydroxy, R20 denotes residue selected from the groups hydrogen, OGlu A few advantageous stilbenes according to formula II are pinosylvin (R18=R19=R20=R15=H, R16=R17=OH), monomethyl ether of pinosylvin (R18=R19=R20=R15=H, R16=OCH$_3$, R17=OH), dihydropinosylvin (R18=R19=R20=R15=H, R16=R17=OH, the phenyl elements bonding ethenyl residue is hydrated to ethyl), resveratrol (R16=R17=R19=OH, R18=R20=H), astringin (R15=R17=OH, R16=R19=H, R18=OH, R20=OGlu and isorhapontine (R16=R19=H, R17=OCH$_3$,R15, R18=OH, R20=OGlu).

Juvabiones refer to compounds according to formula III (Appendix).

Flavonoids refer to compounds according to general formula IV (Appendix), where

R21 denotes residue selected from the groups H, OH,

R22 denotes residue selected from the groups H, OH, =O,

R23 denotes residue selected from the groups H, OH

R24, R25, R26 denote, irrespective of each other, hydrogen or hydroxy,

R26 and R27 denote, irrespective of each other, hydrogen or hydroxy.

Among advantageous compounds according to formula IV are dihydromyricetin (R27=H, R21=R23=R24=R25=R26=R28=OH, R22 is oxo group), taxifolin (R24=R27=H, R21=R23=R25=R26=R28=OH, R22 is oxo group), dihydrokaempferol (R24=R26=R27=H, R21=R23=R25=R28=OH, R22 is oxo group), catechin (R24=R26=R27=H, R21=R23=R25=R26=R28=OH, R22 is hydrogen), naringenin (R23=R24=R26=R27=H, R21=R25=R28=OH, R22 is oxo group), kaempferol (R24=R26=R27=H, R21=R23=R25=R28=OH, R22 is oxo group), teracasidine (R21=R24=H, R22=R23=R25=R26=R27=R28=OH, ketoteracasidine (R21=R24=R26=H, R23=R25=R27=R28=OH, R22 is oxo group), isoteracasidine (R21=R24=R26=H, R22=R23=R25=R27=R28=OH), melacasidine (R21=R24=H, R22=R23=R25=R26=R27=R28=OH), isomelacasidine (R21=R24=H, R22=R23=R25=R26=R27=R28=OH), pinobanxin (R24=R25=R26=R27=H, R21=R23=R28=OH, R22 is oxo group) and pinosembrin (R23=R24=R25=R26=R27=H, R21=R28=OH, R22 is oxo group).

Betulin, by systematic name (IUPAC) lup-20(29)-ene-3β, 28-diol, and its derivatives refer to compounds according to formula 1 E. In the formula 1 E, betulonic acid is compound 2, and betulinic acid is compound 3. Betulin is compound 1. Compounds 2 and 3 are obtained by oxidizing betulin 1 into compound 2, and by reducing compound 2 into compound 3 (U.S. Pat. No. 6,280,778). Betuloinic acid is a derivative of betulonic acid.

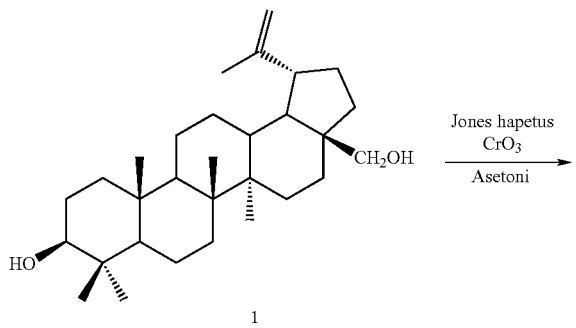

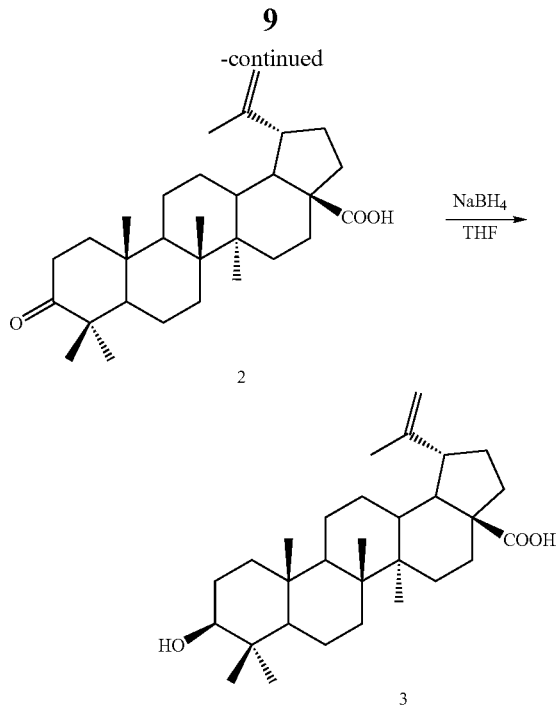

Exemplary oligolignans are beta bound guaiacyl ethers of lignans and stilbenes (trimeric so-called sesquilignans) and coumarates such as secoisolariciresinol guaiacyl glycerol ether, nortrachelogenin guaiacyl glycerol ether, hydroxymatairesinol guaiacyl glycerol ether, lariciresinol guaiacyl glycerol ether, liovile guaiacyl glycerol ethers, conidendrin guaiacyl glycerol ether, pinoresinol guaiacyl glycerol ether, lariciresinol coumarate and secoisolariciresinol coumarate (Willför et al, Holzforchnung, Vol 58, 3435-354, 2004) and dilignans such as 5-5-bis-secoisolariciresinol, 5-5-bis-isolariciresinol, 5-5-bis-lariciresinol.

Depending on the pH, phenolic compounds occur in the compositions either as free, esterized or etherized forms, wherefore also said ester and ether derivatives belong within the scope of the invention.

Free radical here refers to a molecule or an atom that has unpaired electrons in its electron shell. Typical free radicals are oxygen radical, hydroxyl radical and peroxyl radicals as well as superoxide radicals, but also for example lipid radicals. Further, for instance titanium oxide can be formed into a reactive free radical, in case it is tuned to a higher energy state owing to the effect of UV radiation. A compound is called free radical capturer, in case it is capable of inhibiting the creation of free radicals, or their function. In case the compound is capable of inhibiting the creation of particularly oxygenous free radicals and their effects, the compound is called antioxidant.

One of the most important properties of a compound mixture according to the invention is that the compound mixture of phenolic compounds present in the compositions inhibits on a wide scale the growth of antimicrobial agents, when it is added in the composition for 0.1-5 wt %. Generally the amount of synthetic widely antimicrobial agents that can be added to compositions is only roughly 0.01-0.03 wt %, owing to their high cytotoxicity, in case the compositions get into contact with mammal skin at some stage of their usage life. As for Gram-negative bacteria, a compound mixture of phenolic compounds has a growth inhibiting effect is at least against E. coli, Ps. aeruginosa, Ps. putida, and Kl. pneimoniae; as for Gram-positive bacteria, it has a growth-inhibiting effect at least against S. aureus; as for yeasts, it has a growth-inhibiting effect at least against M. furfur and C. albicans, and as for fungi, a growth-inhibiting effect at least against A. niger.

Thus, most of the compound mixtures according to the invention are relatively mild antimicrobial agents, but this is compensated in that owing to their non-toxic nature, they can be used in remarkably larger quantities.

A particular surprising feature in the invention is that although it has been found out that several pure lignan or flavonoid compounds, or knot extracts obtained from trees containing abundantly such lignans or flavonoids, have a limited effect against the growth of micro-organisms, yeasts or fungi, it has not been verified that they should have a wide-scale antimicrobial effect, and they are not effective for example against certain important Gram-positive bacteria such as S. aureus (cf. e.g. Välimaa et al., International J. of Microbiology, 115 (2007) 235-243). Moreover, it has earlier been shown that stilbene-bearing raw extracts and solutions containing refined stilbenes are relatively cytotoxic (e.g. International J. Food Microbiology, 115 (2007) 235-243), which does not encourage a man skilled in the art to use these extracts in cosmetic products. The low cytotoxicity of the compound mixtures according to the invention, combined with low skin irritation and a wide-scale antimicrobial effect, guarantees that the compound mixture according to the invention can be used in sufficiently large quantities, particularly in cosmetic compositions, in order to ensure its antimicrobial effect. The wide-scale antimicrobial effect of the compound mixtures containing phenolic compounds used in the invention, combined with their low cytotoxicity, is a surprising feature, because in the raw extracts obtained from knotty stemwood described in the prior art, their antimicrobial effect has not been verified as particularly wide-scale, not even for raw extracts containing stilbenes.

Further, one of the most important properties of the compound mixtures according to the invention is their minimal penetration to skin, wherefore skin irritation does not occur when using them, as opposite to the conventionally used antimicrobial compounds. The applicant has studied the skin irritation of the compound mixtures according to the invention in a so-called single patch test and found out that they do not irritate the skin with 0.1 wt % contents, and not even with 1 wt % contents; often even 5 wt % contents can be used without excessive skin irritation.

By using the microbial growth inhibiting compound mixture according to the invention, it is often possible to modify the harmful properties of other antimicrobial agents, such as microbicidic and bacteriostatic agents contained in the composition, by reducing the among of free radicals created during their decomposition, and hence the cytotoxicity of these agents.

Among others, the antimicrobial compound mixture according to the invention can be used in cosmetic compositions and their semi-finished compositions, such as sun protection compositions and in semi-finished products used in the manufacturing of sun protection compositions. The compound mixture can also be used in so-called commercial solvents, such as surface treatment agents, solvents used in the cleaning branch solvents etc.

DESCRIPTION OF PREFERRED EMBODIMENTS OF THE INVENTION

One of the advantageous uses of the compound mixture according to the invention is a semi-finished product used in the manufacturing of cosmetic compositions, which is formed of alcohol solvent used as the carrier, and of an antimicrobial compound mixture according to the invention. Several examples of this embodiment are given in the description below.

The compound mixture according to the invention can also be used for technical purposes in various solvents, in liquids used in the machining of metals with chip removal, in cleaning liquids, liquid surface treatment agents, wood preparation fluids, drilling fluids etc. During usage, these liquids may get into contact with human skin, and in that case the microbicidic and bacteriostatic compounds contained therein may cause various allergic reactions, cytotoxic exposure and skin damages. In these technical solutions, the phenolic compounds bearing mixture according to the invention can be used for replacing for example the skin irritative microbicides contained by said solutions, either partly or completely. The compounds contained in the compound mixture have antimicrobial effects, but they do not, however, irritate the skin as much as synthetic antimicrobial agents.

Primarily the effective free radical capturing mechanism of the (poly)phenolic compounds contained in the compound mixture according to the invention appears to be based on the fact that mixture the phenolic compounds contained by the compound mixture go through an automatic oxidization-reduction reaction after neutralizing the free radicals. This automatic oxidization-reduction reaction ends in the formation of stabile dimers. Polyphenol dimers can thereafter be split back to polyphenols (regeneration). A secondary effect of the compound mixtures according to the invention lies in that they are capable of absorbing the UV radiation that creates free radicals, and inhibiting the action of enzymes creating free radicals and/or inhibiting the action of metal ions catalyzing the formation of free radicals, or breaking up hyperoxides. The phenolic compounds contained in the compound mixture according to the invention are well tolerated by mammals, their cytotoxicity is low and they do not themselves form nor induce free radicals.

The production method of a compound mixture according to the invention, and the phenolic compounds contained therein, as well as the mutual ratios of their quantities depend on the designed usage and on the availability of raw materials.

The compound mixtures according to the invention can be isolated from wood material in general. An advantageous raw material source consists of branches, knotwood and knotty stemwood, but also other wood parts, such as stemwood, wood bark and needles can be used.

The compound mixture according to the invention is often obtained from the material of two or more wood species. Thus for example wood processing industry generally uses both spruce and pine in the pulping process. The production of a compound mixture according to the invention can utilize knot wood or knotty stemwood parts that are less suitable in the pulping process. However, because the pulping process mainly uses spruce and to a lesser amount pine, it is often more advantageous to form a compound mixture of spruce, which is more disadvantageous for the use of the composition, because it has better availability than pine. For example, a compound mixture obtained from pine wood knot material in hydrophilic extraction has a remarkably abundant quantity of stilbenes, which are effective microbicides and effective compounds inhibiting microbial growth. As for a compound mixture obtained from spruce wood knot material in a hydrophilic extraction, it contains a remarkable quantity of 7-hydroxymatairesinol, as well as its isomers and derivatives, such as matairesinol. Although the microbicidic efficiency of 7-hydroxymatairesinol is lower than that of stilbenes, particularly that of pinosylvin and its derivatives, it is profitable to use knot extract obtained from spruce, which has better availability and thus generally lower price, in the microbicidic compound mixture.

The phenolic compound mixture according to the invention is produced either by pulverizing or by extracting wood material, or by combining said procedures. Because the wood material most widely available in Finland is pine or spruce, of which particularly the latter contains resin, the extraction is generally realized in two steps. Now resin compounds are extracted from the pulverized pine material, advantageously pulverized knot wood or knotty stemwood material, by a lipophilic extraction solvent, and successively the polyphenols are extracted by a hydrophilic extraction solution. The lipophilic organic extraction solution is for example hydrocarbon, such as lower alkane, for example hexane or heptane. Generally the hydrophilic organic extraction solution is an organic compound containing a carbonyl group, such as alcohol or ketone. Ketone can be used only in case the compound mixture is meant for technical usage. An advantageous ketone is a lower alkyl ketone such as acetone. In case the compound mixture to be produced is a compound mixture in pulverized form, water is removed from the pulverized knotty stemwood material by freeze-drying.

Advantageously the alcohol is a monovalent, bivalent or trivalent lower alkyl alcohol, or a compound mixture of these. The monovalent lower alkyl is preferably ethanol, propanol, butanol, heptanol, octanol or decanol. A compound mixture of a lower alkyl alcohol and glycerol or glycol is an advantageous solvent agent when producing several skin care compositions or semi-finished products of skin care compositions, where the carrier agent is liquid. As for the lower alkylene glycol used as the hydrophilic extraction solution, it is preferably selected from a group comprising propylene glycol, butylene glycol, pentylene glycol and dipropylene glycol. Of these, the latter is particularly advantageous to be used in perfumes. In this kind of extract solution or in an extract concentrate obtained therefrom, the content of alkylene glycol is more than 70 wt %, preferably about 90 wt %.

Extraction of Phenolic Compounds from Wood Material and the Properties of the Extracted Phenolic Compounds The composition of a compound mixture containing phenolic compounds, obtained from one and the same wood material by different extraction methods, fluctuates to some extent. The extraction method is selected according to the target of usage of the composition (for instance use in commercial solvents or cosmetic compositions), and according to the desired antimicrobial properties of the compound mixture. For example from Table 1 below, it can be observed the total quantities of polyphenolic lignan and stilbene compounds contained in pine knotwood and obtained by various extraction methods, as well as the mutual ratios of said polyphenolic compounds, fluctuated to some extent. Moreover, the obtained extract contained a certain amount of resin elements.

TABLE 1

Table 1 illustrates extracts obtained by different extraction methods from pulverized knotty stemwood material of pine (scots pine).

| Compound | Test 1 % of peak | Test 2 % of peak | Test 3 % of peak | Test 4 % of peak |
|---|---|---|---|---|
| PSMME | 16 | 17 | 23 (14) | 29 (16) |
| PS | 15 | 20 | 19 (12) | 20 (12) |
| NTG | 16 | 30 | 30 (18) | 33 (19) |
| Resin acids | 18 | 16 | 12 (7) | 10 (6) |

TABLE 1-continued

Table 1 illustrates extracts obtained by different extraction methods from pulverized knotty stemwood material of pine (scots pine).

| Compound | Test 1 % of peak | Test 2 % of peak | Test 3 % of peak | Test 4 % of peak |
|---|---|---|---|---|
| Oxidized resin acids | 35 | 17 | 17 (10) | 8 (5) |

In all tests 1-4, there were extracted pine chips composed of knotty stemwood. These were first extracted with hexane; in test 4, a technical hexane was used. After the extraction of lipophilic hexane, the samples were extracted with various hydrophilic solutions: in test 1 with acetone, in test 2 with ethanol (96%), in test 3 with acetone and in test 4 again with 96% ethanol. In tests 1 and 4, there were used chips were dead and live wood material were mixed; in tests 2 and 3, the employed wood material consisted of hand-picked dead knotty stemwood chips. After extraction, the quantities of the phenolic and resin compounds contained by the samples were analyzed by liquid-gas-chromatography. The contents of various compounds are given as a percentual area of the peak shown by each compound in relation to the area of all peaks. In tests 3 and 4, the weights of different compounds are given in parentheses with respect to the total weight of the solution.

Abbreviations of the compounds in the Table: PSMME: pinosylvin monomethyl ether (stilbene); PS: pinosylvin (stilbene); NTG: nortrachelogenin (lignan).

It has been discovered that raw extracts from pine knotwood are both microbial growth inhibiting on a wide scale, and also anti-inflammatory, obviously owing to the stilbene compounds contained therein, such as pinosylvin and its derivatives. Thus for example knot extracts containing unrefined phenolic compounds according to Table 1, from tests 1 and 3, can be used as such in commercial solvents. The pine knot extract according to Table 1, obtained from examples 2 and 4, could in turn be used as such as a semi-finished product for manufacturing various cosmetic compositions, without further cleaning, in case the antimicrobial compounds used in said products should be replaced by a compound mixture containing physiologically better tolerated phenolic compounds.

It has been found out that an unrefined extract solution obtained from knotty spruce stemwood material by hydrophilic extraction has, in its spectrum of influence, a similar wide-scale microbial growth-inhibiting effect as extracts obtained from knotty pine stemwood (cf. Table 2 below). Lignans contain mainly hydroxymatairesinol, secoisolariciresinol, conidendrin and oligolignans, as well as smaller amounts of other lignans such as liovile and lariciresinol. Although the microbial growth inhibiting effect of polyphenolic lignan compounds contained in a raw extract obtained from knotty spruce stemwood by alcohol is weaker than with raw extracts obtained from knotty pine stemwood, said extracts obtained from spruce stemwood chips by hydrophilic extraction can be used for producing cosmetic compositions according to the invention and their semi-finished products owing to their low cytotoxic effect and low skin irritation.

TABLE 2A

Polyphenolic compounds contained in a solution extracted from Norway spruce knotty stemwood by pentylene glycol, as defined by a gas-liquid chromatography. The raw extract contained 87-93 wt % pentylene glycol (solvent) and 6.5-7.5 wt % polyphenolic compounds (mainly lignans) extracted from spruce.

| Hydroxymatairesinol | 70-80% |
|---|---|
| Secoisolariciresinol | 3-6% |
| Conidendrin | 4-7% |
| Lariciresinol | 1-3% |
| Liovile | 2-5% |
| Other lignans | 5-8% |

As is seen in Table 2A, spruce contains mainly lignans, of which the majority is hydroxymatairesinol. The other lignans mentioned in the Table 2A are mainly oligolignans. A raw extract extracted from spruce knotwood in alcohol contains mainly lignans and oligolignans (cf. Table 2A above).

In case the extraction methods are changed, lignans can be transformed to other lignans. For example, 7-hydroxymatairesinol can in alkaline extraction conditions be transformed to alpha-conidenrin and further to alpha-conidendric acid or 7-hydroxymatairesinolic acid, and further to isohydroxymatairesinol. In acidic extraction conditions, 7-hydroxymatairesinol is transformed to isohydroxymatairesinol, and alpha-conidendric acid in turn is transformed to cyclolariciresinol, and secoisolariciresinol is in acidic conditions transformed to anhydrosecoisolariciresinol.

Unrefined extracts obtained from knotty pine stemwood by hydrophilic extraction contain a remarkable quantity of stilbene compounds. The applicant has verified that these extracts inhibit the growth of micro-organisms (Gram-positive and negative bacteria, fungi and yeasts) in a wide scale. Thus, pine is a good source of the antimicrobial compound mixtures according to the invention. It has also been discovered that stilbenes have anti-inflammatory properties. On the other hand, unrefined raw extracts obtained from spruce contain mainly lignans; the applicant has verified that said lignans have, by their spectrum of influence, a similar but weaker effect for inhibiting the growth of micro-organisms than stilbene-bearing raw extracts obtained from pine. Both raw extracts extracted from knotty pine stemwood and containing mainly stilbenes, as well as raw extracts extracted from knotty spruce stemwood and containing mainly lignans, are feasible when manufacturing different compositions that have a wide-scale antimicrobial effect and at the same time low skin irritation and low cytotoxicity in comparison with BHT.

From the pulping processes of wood processing industry, there is obtained remarkably more spruce than pine, which fact is in favor of a solution that the compound mixtures according to the invention comprise compound mixtures of unrefined extraction solutions obtained from spruce by hydrophilic extraction, or unrefined extraction solutions obtained from spruce and pine by hydrophilic extraction. In a suitable arrangement, the combined extraction solutions according to the invention contain for example 70 wt % (poly)phenolic compounds (lignans and oligolignans) extracted from knotty spruce stemwood, and 30 wt % (poly)phenolic compounds extracted from knotty pine stemwood, with stilbenes included. Other mixture ratios can also be applied, as long as it is taken care of that the compound mixture contained in the combined extraction solution obtained from pine and spruce has a sufficiently low cytotoxicity (the employed reference is BHT).

The applicant has discovered that when the mutual mixing ratios of the raw extracts obtained from different wood species are selected so that the cytotoxicity for the powdered or extracted compound mixture, expressed as wt % from total content of the end composition, when measured in ethanol for a HaCat cell culture after 24 incubations, is lower than the cytotoxicity of 0.02-0.1 wt % BHT % from total content of the end composition dissolved in ethanol in the same incubation conditions, preferably lower than the cytotoxicity of 0.01 -0.05 wt % BHT % from total content of the end composition dissolved in ethanol in the same incubation conditions, the allowed quantity for the employed mixture is 0.1-5 wt % of the total weight of the end composition, in most cases 1-5 wt % of the total weight of the end composition. This limit value of the content is remarkably higher than with most commercially available wide-scale, microbial growth inhibiting synthetic substances, which means that the compound mixtures according to the invention can be used in sufficient quantities for ensuring their wide-scale antimicrobial effect.

Hardwood species contain remarkable quantities of different flavonoids, biflavonoids and flavonoid glycosides, as is apparent from Table 2B below. Unrefined raw extracts containing flavonoids, obtained from hardwood species, have antioxidative and free radical capturing properties, wherefore they can be used for example together with raw extracts obtained from knotty pine or spruce stemwood for producing compound mixtures containing phenolic compounds according to the invention, as well as their intermediate products.

Mixture according to the invention can be isolated from wood material in general. An advantageous raw materia source consists of wood branches and stem's knotwood parts, but also othet wood parts, such as stemwood, wood park and needles can be used.

TABLE 2B

The principal components of unpurified extraction solutions obtained by hydrophilic extraction from knotty stemwood of various hardwood species.

| *Acacia crassicarpa* | |
|---|---|
| Flavonoids | 54% |
| Melacasidine | 24% |
| Isomelacasidine | 18% |
| Biflavonoids | 9% |
| *Acacia mangium* | |
| Flavonoids | 36% |
| Teracasidine | 25% |
| Ketoteracasidine | 3% |
| Biflavonoids | 8% |
| *Fagus sylvatica* | |
| Flavonoids | |
| Catechin | 6% |
| *Eucalyptus globulus* | |
| Tannins | 19% |
| Tannin monemers | 5% |
| Ellagic acid | 3% |
| Gallic acid | 2% |
| *Populus grandidentata* | |
| 54% Flavonoids | 31% |
| Dihydrokaempferol | 13% |
| Catechin | 9% |
| Naringenin | 7% |
| Taxifolin | 3% |
| Flavonoid glycosides | 34% |
| *Populus tremula* | |
| 36% Flavonoids | 21% |
| Dihydrokaempferol | 17% |
| Naringenin | 3% |
| Flavonoids glycosides | 8% |

TABLE 2B-continued

The principal components of unpurified extraction solutions obtained by hydrophilic extraction from knotty stemwood of various hardwood species.

| *Populus tremuloides* | |
|---|---|
| 7% Flavonoids | 23% |
| Dihydrokaempferol | 17% |
| Naringenin | 10% |
| Kaempferol | 1% |
| Taxifolin | 1% |
| Flavonoid glycosides | 24% |

Compounds isolated from wood bark are enlisted in Table 3A and in FIG. 1 illustrates compounds isolated specifically from birch bark.

As can be observed for example from Table 3A, extracts obtained from the bark of different wood species by hydrophilic extraction contain various polyphenolic flavonoid compounds. In the present invention, these unrefined extracts mainly containing flavonoids can be used either as such or preferably together with hydrophilic extracts obtained from other the material of wood species, to be further used for producing various compositions according to the invention and their semi-finished products. One source of these advantageous flavonoids is the bark of birch (*Pendula betula*).

TABLE 3A

Principal components of unrefined extraction solutions obtained from the bark of different wood species by hydrophilic extraction (Extractives in stemwood and knots of Acasia and Aspen trees, Suvi Pietarinen, Abo Akademi, Turku 2005).

*Thuja occidentalis*

Sugars
Catechin
Isorhapontine
Astringin
Tannins

*Pinus banksiana*

Sugars
Taxifolin
Isorhapontine
Dihydromyrcetin
Tannins

*Betula pendula*

Betuligenili glycoside
Catechin
Sugars
Tannins

*Pseudotsuga menziensii*

Sugars
Taxifolin
Catechin
Tannins

*Picea abies*

Isorhapontine
Astringin
Resvatrol-glycoside
Tannins

*Abies lasiocarpa*

Sugars
Resin acids
Tannins

*Populus tremula*

Undefined glycosides
Tannins

TABLE 3A-continued

Principal components of unrefined extraction solutions obtained from the bark of different wood species by hydrophilic extraction (Extractives in stemwood and knots of Acasia and Aspen trees, Suvi Pietarinen, Abo Akademi, Turku 2005).

*Pinus mariana*

Sugars
Catechin
Tannins

FIG. 1
FIG. 1 illustrates the different phenolic and polyphenolic compounds contained in the bark of betula pendula (birch tree).

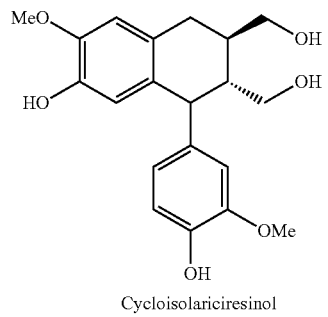

Cycloisolariciresinol

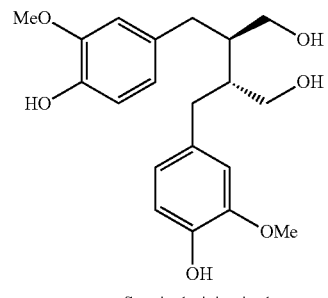

Secoisolariciresinol

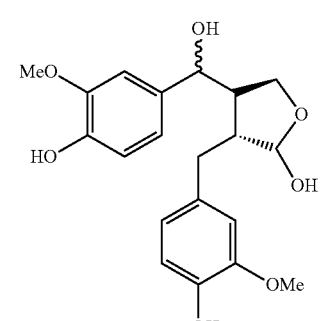

Isoliovil

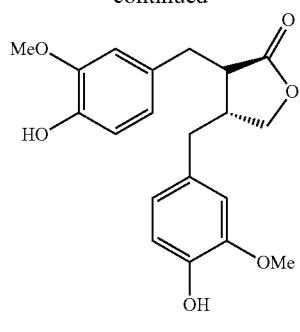

Matairesinol

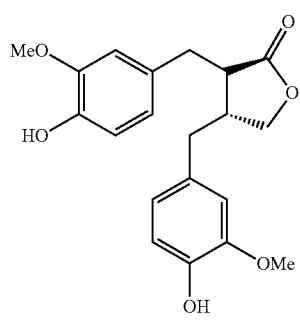

Matairesinol

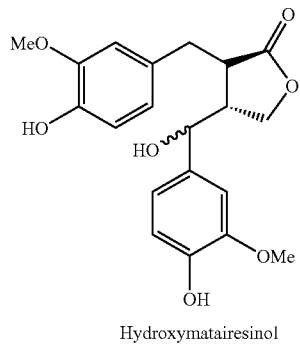

Hydroxymatairesinol

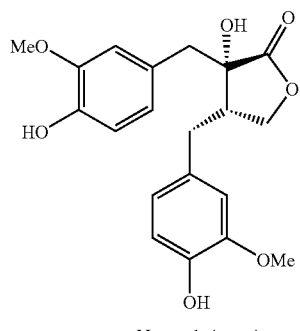

Nortrachelogenin

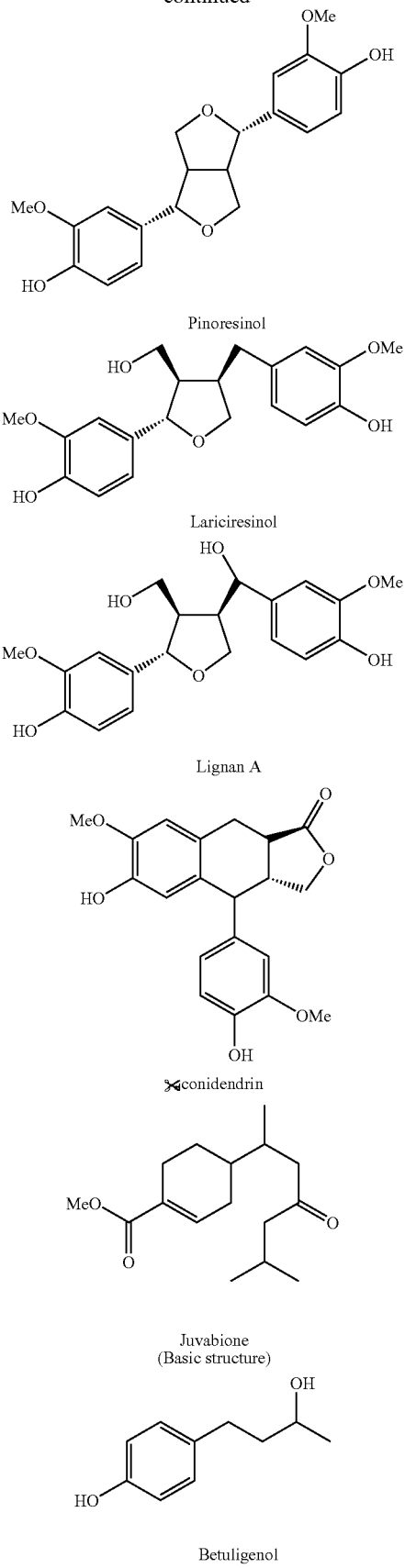

As can be observed from FIG. 1 birch bark contains lignans, stilbenes, flavonoids, juvabiones and betuligenol and its derivatives, wherefore it can also be used as a raw material for producing an antimicrobial compound mixture according to the invention. Betuligenol (betulin) mentioned at the end of FIG. 1 as well as its derivatives betulinic acid, betuloinic acid or betulonic acid, can also be used in compound mixtures according to the invention, either as separately added therein in refined form, or together with an unrefined compound mixture obtained from birch bark extraction.

TABLE 3B

Principal components of unrefined extracts obtained from the knotty stemwood of a few pine and spruce species by hydrophilic extraction (Wilför et al., J. Agric. Food. Chem., 51, 26 (2003)), in percentages by weight of the total quantity of the components of the compound mixture extracted from the wood.

| Wood material | Compounds | wt % |
|---|---|---|
| *Picea abies* | | |
|  | Lignans | 53 |
| hydroxymatairesinol |  | 41 |
| secoisolariciresinol |  | 3 |
| α-conidendrin |  | 7 |
| Oligolignans |  | 12 |
| *Abies sibirica* | | |
|  | Lignans | 33 |
| secoisolariciresinol |  | 21 |
| lariciresinol |  | 7 |
| Oligolignans |  | 31 |
|  | Juvabiones | 3 |
| *Abies balsamea* | | |
|  | Lignans | 22 |
| secoisolariciresinol |  | 18 |
| lariciresinol |  | 9 |
|  | Oligolignans | 19 |
|  | Juvabiones | 2 |
| *Pinus sibirica* | | |
|  | Lignans | 26 |
| lariciresinol |  | 19 |
| isolariciresinol |  | 3 |
| secolariciresinol |  | 2 |
| Oligolignans |  | 6 |
|  | Flavonoids | 7 |
| pinosembrin |  | 6 |
|  | Stilbenes | 25 |
| dihydropinosylvin monomethyl ether |  | 15 |
| pinosylvin |  | 3 |
| dihydropinosylvin |  | 2 |
| *Pinus contorta* | | |
|  | Lignans | 10 |
| nortrachelogenin |  | 5 |
| liovile |  | 3 |
| oligomers |  | 3 |
|  | Flavonoids | 20 |
| pinosembrin |  | 15 |
| pinobanxin |  | 7 |
|  | Stilbenes | 15 |
| Pinosylvin monomethyl ether |  | 9 |
| Pinosylvin |  | 6 |

In FIG. 2 below is introduced polyphenolic compounds present in pine.

FIG. 2
FIG. 1 illustrates different phenolic compounds that can be obtained by a hydrophilic extraction of wood material originated to knotty stemwood or bark of pine.
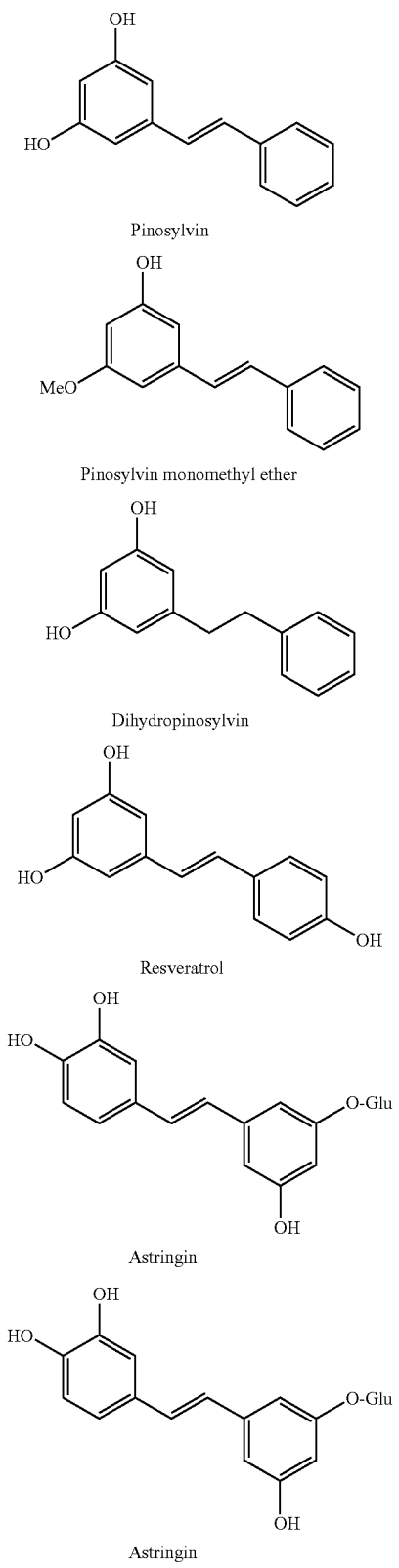
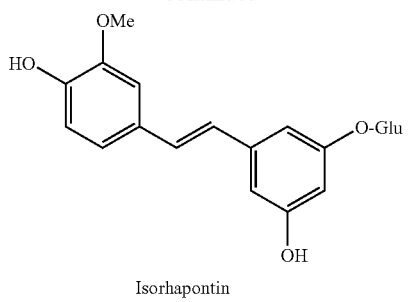
Isorhapontin
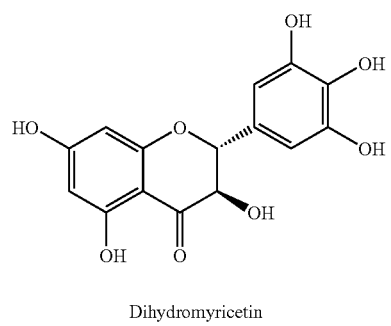
Dihydromyricetin
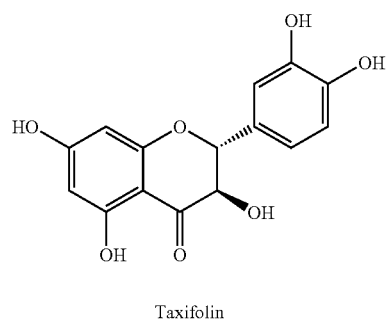
Taxifolin
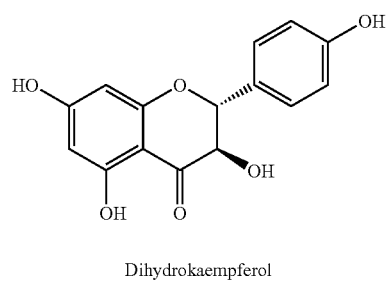
Dihydrokaempferol
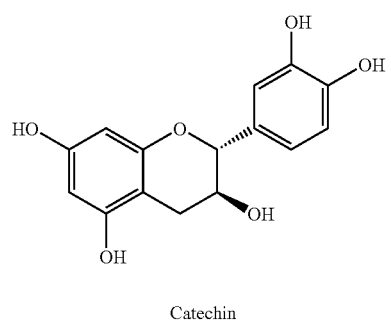
Catechin

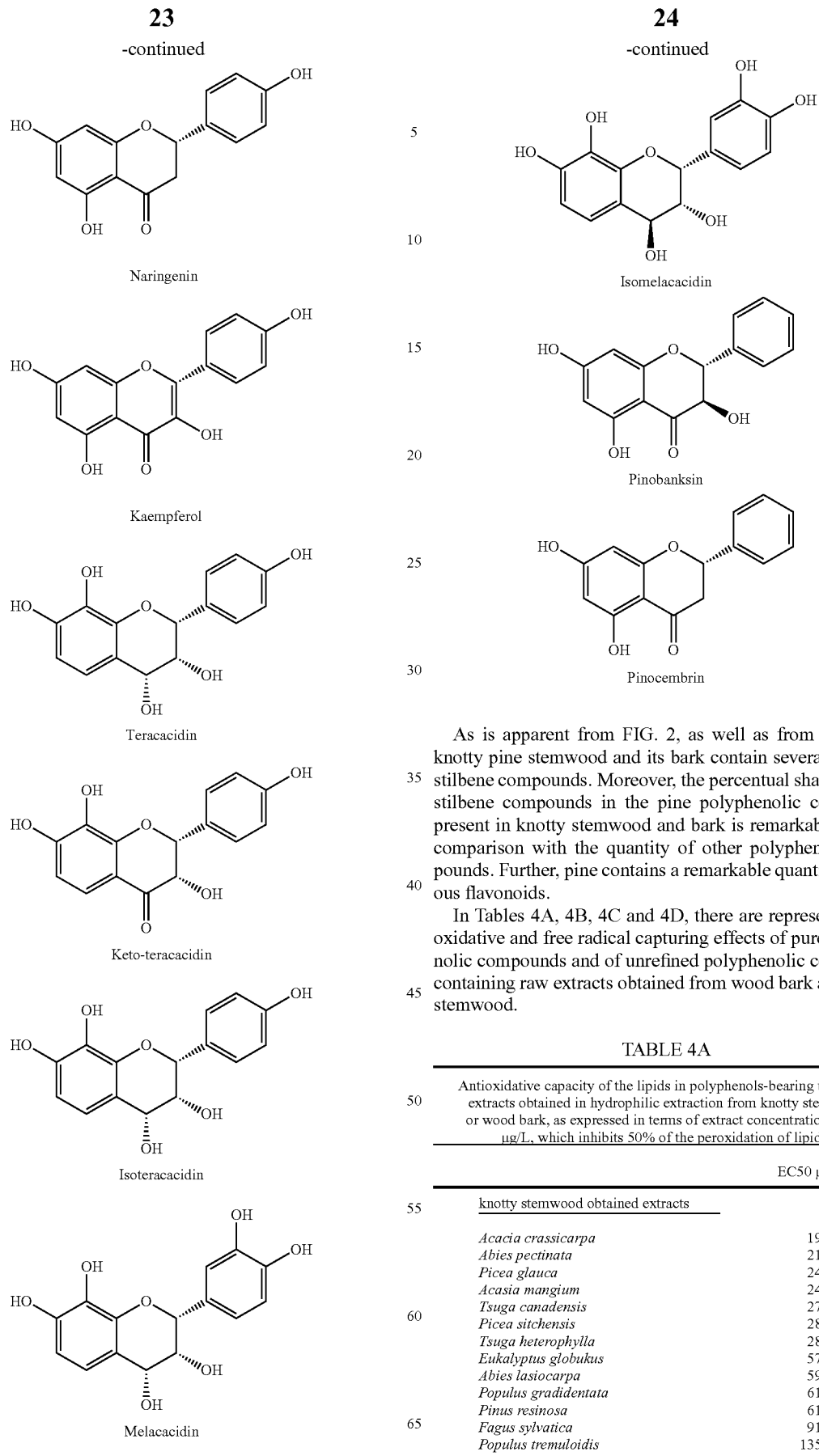

As is apparent from FIG. 2, as well as from Table 4B, knotty pine stemwood and its bark contain several different stilbene compounds. Moreover, the percentual share of these stilbene compounds in the pine polyphenolic compounds present in knotty stemwood and bark is remarkably high in comparison with the quantity of other polyphenolic compounds. Further, pine contains a remarkable quantity of various flavonoids.

In Tables 4A, 4B, 4C and 4D, there are represented antioxidative and free radical capturing effects of pure polyphenolic compounds and of unrefined polyphenolic compounds containing raw extracts obtained from wood bark and knotty stemwood.

TABLE 4A

Antioxidative capacity of the lipids in polyphenols-bearing unrefined extracts obtained in hydrophilic extraction from knotty stemwood or wood bark, as expressed in terms of extract concentration EC50 μg/L, which inhibits 50% of the peroxidation of lipids.

| | EC50 μg/L |
|---|---|
| knotty stemwood obtained extracts | |
| Acacia crassicarpa | 19 |
| Abies pectinata | 21 |
| Picea glauca | 24 |
| Acasia mangium | 24 |
| Tsuga canadensis | 27 |
| Picea sitchensis | 28 |
| Tsuga heterophylla | 28 |
| Eukalyptus globukus | 57 |
| Abies lasiocarpa | 59 |
| Populus gradidentata | 61 |
| Pinus resinosa | 61 |
| Fagus sylvatica | 91 |
| Populus tremuloidis | 135 |

TABLE 4A-continued

Antioxidative capacity of the lipids in polyphenols-bearing unrefined extracts obtained in hydrophilic extraction from knotty stemwood or wood bark, as expressed in terms of extract concentration EC50 µg/L, which inhibits 50% of the peroxidation of lipids.

|  | EC50 µg/L |
|---|---|
| Pinus strobes | 159 |
| Populus tremula | 317 |
| extracts obtained from wood bark |  |
| Picea abies | 49 |
| Betula pendula | 81 |
| Pycnogenol | 84 |
| Pseudotsugamenziensii | 84 |
| Thuja occidentalis | 131 |
| Pinus banksiana | 143 |
| Populus tremula | 213 |
| Abies lasiocarpa | 316 |

TABLE 4B

Comparison of the antioxidative capacity of the lipids in pure polyphenol extracts isolated from certain wood materials, as expressed by the extract concentration EC50 µg/L, which inhibits 50% of the peroxidation of the lipids.

| Compound | EC50 µg/L |
|---|---|
| Cyclolariciresinol | 17 |
| Pinoresinol | 20 |
| Melacasidine | 36 |
| Secoisolariciresinol[1] | 37 |
| Taxifolin[1] | 46 |
| Pinosylvin | 50 |
| Teracasidine | 50 |
| Nortrachelogeniini[1] | 53 |
| Hydroxymatairesinol[1] | 58 |
| Matairesinol[1] | 99 |
| Lariciresinol[1] | 126 |
| Dihydrokaempferol | 488 |
| Pinosembrin | 1135 |

[1]Willför et al,. J. Agric. Food. Chem, 51. 26 (2003).

Tables 4C and 4D further represent the free radicals capturing capacity of certain pure polyphenols and unrefined polyphenol extracts with respect to peroxide radicals.

TABLE 4C

Peroxide radicals/(mmol) capturing capacity of unrefined polyphenols-bearing extracts obtained in hydrophilic extraction from knotty stemwood or wood bark, as expressed in capacity per gram of extract.

| extracts obtained from knotty stemwood | Wood material, capturing capacity mmol/g |
|---|---|
| Acacia crassicarpa | 21 |
| Eucalyptus globulus | 7.8 |
| Picea glauca | 7.8 |
| Abies pectinata | 6.8 |
| Tsuga canadensis | 6.8 |
| Acasia mangium | 6.8 |
| Tsuga heterophylla | 5.8 |
| Larix lariciana | 5.8 |
| Larix sibrica | 5.8 |
| Picea mariana | 5.8 |
| Picea sitchensis | 4.9 |
| Pinus sylvestris | 4.9 |
| Thuja plicata | 3.9 |
| Populus gradidentata | 3.9 |
| Fagus sylvatica | 2.9 |
| Abies lasiocarpa | 2.7 |
| Pinus resinosa | 2.7 |

TABLE 4C-continued

Peroxide radicals/(mmol) capturing capacity of unrefined polyphenols-bearing extracts obtained in hydrophilic extraction from knotty stemwood or wood bark, as expressed in capacity per gram of extract.

| Pinus banksiana | 1.9 |
|---|---|
| Pinus strobus | 1.1 |
| Populus tremuloides | 0.39 |
| Populus tremula | 0.29 |
| wood bark obtained extracts | mmol/g |
| Pseudotsuga menziensii | 4.9 |
| Pycnogenol | 4.9 |
| Pinus banksiana | 3.1 |
| Betula pendula | 2.9 |
| Picea abies | 2.9 |
| Thuja occidentalis | 1.9 |
| Abies lasiocarpa | 0.58 |
| Populus tremula | 0.29 |

TABLE 4D

Comparison of the peroxide radicals (mmol) capturing capacity of certain pure polyphenol extracts isolated from wood material, as expressed per gram of extract.

| Compound | capturing capacity mmol/g |
|---|---|
| Melacasidine | 20 |
| Taxifolin[1] | 16 |
| Cyclolariciresinol | 12 |
| Secoisolariciresinol[1] | 8.5 |
| Pinoresinol | 7.8 |
| Tetra casidin | 7.8 |
| Nortrachelogenin[1] | 5.9 |
| Hydroxymatairesinol[1] | 5.6 |
| Matairesinol[1] | 2.9 |
| Lariciresinol[1] | 2.7 |
| Dihydrokaempferol | 0.78 |
| Pinosylvin | 0.78 |
| Pinosembrin | 0.49 |

[1]Willför et al,. J. Agric. Food. Chem., 51, 7600-7606 (2003).

Tables 4A and 4B represent the antioxidative effect of a few pure polyphenols and of unrefined polyphenolic compounds containing raw extracts, obtained from wood bark and knotty stemwood. Tables 4C and 4D in turn illustrate the peroxide radicals capturing capacity of a few pure polyphenols and of unrefined, polyphenolic compounds containing raw extracts, obtained from wood bark and knotty stemwood. In Tables 4A-4D, it can be observed that the antioxidative and free radical capturing properties of solutions containing pure polyphenol compounds, obtained from wood material in hydrophilic extraction, are often remarkably different from the corresponding properties of compound mixtures containing unrefined raw extract solutions and obtained from wood material in hydrophilic extraction, owing to the synergetic effects of the compounds contained in the compound mixtures in unrefined extracts. The compound mixtures according to the invention are obtained from these unrefined raw extract solutions.

Production of the Compositions and Their Semi-finished Products

A phenolic compounds containing mixture according to the invention can be included in cosmetic and food technology compositions and their semi-finished products in a way known as such, of which examples are also given below. Thus, in case a compound mixture is extracted for instance of wood material by an alcoholic solution into a raw extract, this raw extract can be made into a homogeneous mixture such as a homogeneous solution, or a colloidal dispersion with two or several phases such as gel, paste, emulsion, microemulsion, nanoemulsion suspension, dispersion or mist. In that case a phenolic compounds containing raw extract is included in a homogeneous solution by dissolving, and/or it is included by dispersing to the carrier agents of a colloidal mixture in a way known as such, so that the raw extract is admixtured either in a phase containing a continuous carrier agent, or to a phase containing a carrier agent to be dispersed. For forming a carrier of carrier agents, there are is used conventional auxiliary agents of the trade. Such agents are, among others, surface active agents, dispersing agents such as emulsifying agents, gel formers such as carbomers and methylcellulose.

The employed carrier agents are gel base formers such as water or alcohol, cream base and paste base formers such as paraffins, waxes, silicones, aqueous phase forming agents (water) or phase formers such as paraffin or stearic acid. The compositions can also be multi-phase compositions, so that the carrier agent is formed of several aqueous and/or oil phases. With respect to the manufacturing of various compositions, we refer to the literature of this field and to the examples to be given below.

In these homogeneous solutions and colloids, there can be admixtured additives such as UV protective agents, antioxidants and vitamins, surface active agents, moisturizing agents, moisture maintaining agents, stabilizing agents, moisture absorbing agents, emollients, fats, lubricants, perfumes, viscosity regulators, colorants, antioxidants and narrow-scale antimicrobial agents etc., in a conventional way known as such, with respect to which we refer to the literature of of this field.

In case the composition is a packing material composition, the carrier agent is a packing material, in which the compound mixture contained in the extraction solution is impregnated or spread on. Said packing material can be cardboard, corrugated board, plastic admixtured cardboard or other packing material known from the prior art.

In case the composition is a technical composition, the carrier is a commercial solvent, cleaning device such as a cleaning cloth, solid substance such as a powder used as a surface treatment agent, or a solution meant for the cleaning of a mammal's body. In the carrier, there is impregnated or otherwise included the compound mixture according to the invention.

Surface active agents applicable in exemplary liquid compositions according to the invention, and in their semi-finished compositions are: tensides, lecithin, caprylic acid and monoglycerides and diglycerides of capric acids, polyglyceryl-3-di-isostearate/polyglyceryl-2 and polyhydroxystearate, alkyl glycoside/alkyl alcohol, cetearyl pyridium chloride, bentsalkonium chloride, ionogenic agents, cetearyl glycosides, lower alcoxilated glycosides and micelle-forming agents.

Perfumes can be selected for example from a group including phenyl ethyl glycol, eugenol, isoeugenol, geraniol, citronellol or linalool, or their esterized forms or their aldehydes.

Colorants can be selected for example from among the colorants accepted by FDA to be used in foodstuffs and cosmetic products.

In compositions according to the invention, as well as in their semi-finished products, it is also possible to add other effective agents as additives. Such effective agents to be used as additives are for example antioxidants. Among antioxidants, let us point out natural and synthetic vitamins such as vitamin A, B, C. D, E, provitamin B5, vitamin B3, L-ascorbic acid and vitamin E; further, there can be used antioxidants obtained from natural sources, such as antioxidants contained in green tea, antioxidants contained in flaxseed, antioxidants contained in horse chestnut, beta carotene, selenium, glutamine, ubiquinone (coenzyme Q10), glycolic acid, growth hormones and kinetin.

An advantageous botanical microbial growth inhibiting agent is betulinic acid, betuloinic acid or betulonic acid (U.S. Pat. No. 6,280,778), derivatives of betuligenolin, and resvatrol obtained from spruce bark. These have been found to have an antimicrobial effect, and their cytotoxicity for healthy cells is low, and they enhance the dying of cancer cells. These can be added, either as pure compounds or as unrefined extract solutions obtained from wood bark, or as powders, in compositions and semi-finished products to be manufactured according to the invention.

Further, in compositions to be manufactured according to the invention, there can also be added pure flavonoids, lignans and stilbenes as well as their oligomers isolated from plants. In this application, the term 'oligomers' refers to homologs of a compound, i.e. to its dimers, trimers etc., where the included number of similar units is lower than in a polymer. Suitable botanical polyphenol compound sources are oilseeds, nuts, grain, fruits, berries and pulses.

EXAMPLES

Field Tests
A) Cytotoxicity in Comparison with BHT

Table 1 shows comparisons between the cytotoxicity of a compound mixture according to the invention and the cytotoxicity of an antioxidant (BHT) that is widely used in food and cosmetic industry.

TABLE 5

The cytotoxicity of sample extracts pulverized or alcohol-extracted of knotty spruce stemwood chips, containing the compound mixture, or a powder containing the compound mixture, in comparison with the cytotoxicity of BHT (butylated hydroxytoluene). The composition of the individual compounds included in the compound mixture contained by the samples was in accordance with Table 2A. The cytotoxicity of the sample extracts and powders for human keratinocyte cells was measured. The employed measure of cytotoxicity was the total protein quantity created by the samples, when the samples were incubated together with human keratinocyte cells for a certain incubation time (24 h). For each sample, there was searched a limit value (EC20), by which 20% of the cultivated cells died.

| Extraction solvent | sample | EC20 ppm 24 h |
|---|---|---|
| pentylene glycol | HMR-5 | 450 |
| butylene glycol | HMR-4 | 600 |
| glycerol | HMR | 1.260 |
|  | HMR powder | 160 |
| propylene glycol | HMR-3 | 620 |
| ethanol | HMR extract | 550 |
| ethanol | BTH | 5.50 |

From Table 5c it can be observed that the most cytotoxic substance was BTH, which was 10-20 times more cytotoxic than HMR powder. HMR powder was obtained by pulverizing knotty spruce stemwood chips without other further cleaning, and said powder contained mainly 7-hydroxymatairesinol as well as, to a lesser degree, other polyphenolic lignans. Other knot extracts obtained from spruce knotwood chips by hydrophilic extraction with alcohol (ethanol, propylene glycol, pentylene glycol, butylene glycol, or glycerol) also contained lignan mixtures according to the invention, which included, as their principal component, 7-hydroxymatairesinol and also other phenolic lignans. With respect to HMR extract mixtures, BTH was 50-100 times more cytotoxic.

B) Antimicrobial Effect

Test 1

The antimicrobial effect of a few compound mixtures according to the invention against bacteria, yeast and fungi was examined:

raw extracts extracted from knotty spruce stemwood chips by 4-glycol (sample 1), 5-glycol (sample 2) and 3), glycerine (sample 3) and glycerol (sample 4), containing 10 wt % of the compound mixture, the composition of the polyphenolic compounds of said raw extracts being in accordance with Table 2A (contained most 7-hydroxymatairesinol).

combined raw extract (sample 5), extracted of knotty spruce stemwood chips and knotty pine stemwood by ethanol (pine) and by butylene glycol (spruce), containing roughly 10 wt % of the compound mixture obtained from pine and spruce. The sample mixture contained both a lignan mixture obtained from Norway spruce (*Picea abies*), the composition of which was in accordance with Table 2A, and a compound mixture of lignans and stilbenes obtained from pine (*Pinus sylvestris*), the composition of which roughly corresponded to the one illustrated in Table 1 (test 2, ethanol extraction).

The growth-inhibiting effect of the compound mixture samples was verified against the following micro-organisms:

*Staphylococcus aureus* ATCC 6538
*Esterichia coli* ATCC 8739
*Pseudamonas auriginosa* ATCC 9027
*Psudomonas putida* ATCC 49128
*Klebsiella pneumoniae* ATCC 10031
*Candida albicans* ATCC 10231
*Malassezia furfur* ATCC 96809 (yeast fungus)
*Aspergillus niger* ATCC 16404

Performance of the Study

In each of the 10 g sample batches taken from the samples, there were added different microbe cell suspensions, where the microbe population density was at least $5\times10^6$ microbes/ml. The sample batches were incubated at room temperature (22° C.) for 2, 4, 24 and 48 hours, 4 days, 7 days, 14 days and 28 days.

When reproductive microbes were not found in the samples anymore, each sample was cultivated for a 1 ml sample batch in a 100 ml Letheen broth base, and after concentration, possible bacterial growth was further checked on a culture base.

Results

All samples had an extremely good antimicrobial effect; after an incubation time of 4 hours, 24 hours, 48 hours, 7 days, 14 days and 28 days, microbial growth was not detected.

Both the raw extracts obtained from spruce material according to the invention by alcohol extraction, and the raw extracts obtained from pine material by alcohol extraction, as well as the raw extracts obtained from a combined spruce and pine material by alcohol extraction prevented the growth of antimicrobial agents on a wide scale. They prevented the growth of both Gram-negative bacteria *E. coli, Ps. aeruginosa, Ps. putida, Kl. pneimoniae*) and Gram-positive bacteria (*S. aureus*). In addition, they also efficiently prevent the growth of yeasts (*M. furfur, C. albicans*) and fungi (*A. niger*).

Test 2

Raw extract extracted from knotty spruce stemwood with pentylene glycol, containing a 10 wt % mixture of phenolic compounds, the composition of which was in accordance with Table 2A, was added in a sun protection cream for 3 wt %. Ethylhexyl glycerine (EH), efficient against Gram-positive bacteria was mixed into same sun protection cream for 0.3 wt % and 0.5 wt %. For the sake of comparison, to the same sun protection creams there was added a conventionally used, widely anti micro-organistic agent, phenoxyethanol (FE), which has a relatively low highest acceptable quantity of usage owing to its cytotoxicity and skin irritative properties.

| | number of inoculation cycles | | | | | | |
|---|---|---|---|---|---|---|---|
| Test | 0 | 1 | 2 | 3 | 4 | 5 | 6 |
| Test 1 cream base 0.3 wt % EH 1 wt % FE | − | − | − | +Y | +M, Y | +M, Y | ++M, Y |
| Test 2 Cream base 0.5 wt % FE 1 wt % EF | − | − | − | − | − | − | − |
| Test 3 Cream base 0.3 wt % EH 3 wt % HMR-5 | − | − | − | − | − | − | − |
| Test 4 Cream base 0.3 5-% EH 3 wt % HMR-5 | − | − | − | − | − | − | − |

Y = yeast growth
M = Fungal growth
− no microbial growth
+ slight microbial growth
++ moderate microbial growth As is apparent from the above described test 2, when a 3 wt % raw extract containing about 10 wt % of compound mixture, obtained from knotty spruce stemwood was used in a sun protection cream instead of phenoxyethanol, it was possible to maintain a wide-scale antimicrobial effect. The effect was maintained, although the content ethylhexyl glycerine, inhibiting the growth of Gram-positive bacteria, was reduced, which shows that the raw extract from knotty spruce stemwood itself has a Gram-positive bacteria growth-inhibiting effect.

The sun protection cream used in the above described test was a cream according to example 2. When using phenoxyethanol, the highest acceptable content of which is 1 wt %, there was detected a growth of yeasts and fungi with an ethylhexyl glycerine content of 0.3 wt % in the sun protection cream. On the other hand, with an ethylhexyl glycerine content of 0.5 wt %, the growth of yeasts and fungi was inhibited. When phenoxyethanol was replaced by a lignan mixture HMR-5 obtained from knotty spruce stemwood with hydrophilic extraction (pentylene glycol), it was observed that the ethylhexyl glycerine content could be reduced to 0.3 wt %, and yet the microbial growth in the cream was inhibited. Thus the alcohol extract (HMR-5) according to the invention, which contains a physiologically well-tolerated phenolic compound mixture, can be used to replace the antimicrobial phenoxyethanol, the use of which is restricted owing to its physiological toxicity. The composition HMR-5 was in accordance with the composition according to Table 2A.

Production of the Compositions and Their Semi-finished Products

Example 1

Example 1 describes an antimicrobial composition (semi-finished product), in which there is used an unrefined solution obtained by hydrophilic extraction from Norway knotty spruce stemwood material.

Semi-finished Product

Ethylhexyl glycerine, antimicrobial compound 1 part Raw wood knot extract obtained by pentylene glycol extraction from knotty stemwood chips of Picea abies (Norway spruce) 6 parts The extract obtained from Norway spruce contained a compound mixture of phenolic compounds, where the composition of the phenolic compounds was in accordance with Table 2A. Ethylhexyl glycerine is efficient against Gram-negative bacteria, and it also has skin moisturizing and softening properties, wherefore it is used, among others, in deodorants for roughly 0.2-2 wt % solution of the total weight. Ethylhexyl glycerine is neither effective against Gram-positive bacteria, nor yeasts or fungi, and for this purpose there is therefore generally used another compound that is widely inhibiting for microbial growth, such as phenoxyethanol, which has a synergic positive effect with ethylhexyl glycerine. Phenoxyethanol is toxic, allergenic and skin irritative, and its highest acceptable limit of usage is roughly 1 wt % of the total weight of the composition.

A semi-finished product composed of ethylhexyl glycerine and a widely antimicrobial raw extract obtained in hydrophilic extraction from knotty stemwood material, which contains the compound mixture according to the invention, can be used in the same targets of usage as the known ethylhexyl glycerine and phenoxyethanol combination. Typical targets of usage are sun protection products, deodorants and cleaning cloths impregnated by the compound mixture.

Example 2

UVA/UVB Sun Protection Lotion, O/W type, with TINOSORB® M

Lotion with a very high SPF and excellent UVA protection due to the photostable UVA filter TINOSORB® M. This emulsion is smooth and spreads easily. SPF in vivo=38, broadband.

This lotion includes phenonip (various parabens) as a narrow-scale antimicrobial agent. Parabens are effective against fungi and bacteria. By using extract from wood knots containing mixture of phenolic compounds in glycerine the amount of phenonip can be diminished.

Composition

|  | Trade name | Inci Name | Supplier | % w/w (as supplied) |
| --- | --- | --- | --- | --- |
| Part A | Amphiosol K | Potassium Cetyl Phosphate | Roche | 2.00 |
|  | Antaron WP-660 | Tricontanyl PVP | ISP | 1.00 |
|  | Myritol 318 | Caprylic/Capric Triglyceride | Cognis | 5.00 |
|  | Crodamol AB | C12-15 Alkyl Benzoate | Croda | 5.00 |
|  | Cetiol SN | Cetearyl Isononanoate | Cognis | 5.00 |
|  | Cutina GMS | Glyceryl Stearate | Cognis | 3.00 |
|  | Lanette 16 | Cetyl Alcohol | Cognis | 1.00 |
|  | Dow Corning 200 Fluid 350 cs | Dimethicone | Dow Corning | 0.10 |
|  | TINOSORB ™ OMC | Ethylhexyl Methoxycinnamate | Ciba Specialty Chemicals | 5.00 |
| Part B | Water | Water |  | q.s. to 100 |
|  |  | 10% Extracted Spruce and/or Pine knot mixture in Glycerine | Granula Ltd | 3.00 |
| Part C | SALCARE ® SC80 | Steareth-10 Allyl Ether/Acrylates Copolymer | Ciba Specialty Chemicals | 0.50 |
| Part D | TINOSORB ® M | Methylene Bis-Benzotriazolyl Tetramethylbutylphenol (and) Aqua (and) Decyl Glucoside (and) Propylene Glycol (and) Xanthan Gum | Ciba Specialty Chemicals | 20.00 |
| Part E | Phenonip | Phenoxyethanol (and) Methylparaben (and) Ethylparaben (and) Butylparaben (and) Propylparaben (and) Isobutylparaben | Clariant | 0.30 |
| Part F | Sodium Hydroxide (Solution 10%) | Water (and) Sodium Hydroxide |  | q.s. to pH 7.00 |
| Part G | Fragrance | Fragrance |  | q.s. |

Technical Data

| | |
|---|---|
| pH value | 7.00 |
| Appearance | white lotion |
| Viscosity (Brookfield DVIII + LV4/80 rpm) | 3000 mPas |
| UVA/UVB ratio*/Critical Wavelength* | 0.75/384 nm |

Technical Data

| | |
|---|---|
| pH value | 7.00 |
| Appearance | white lotion |
| Viscosity (Brookfield DVIII + LV4/80 rpm) | 3000 mPas |
| UVA/UVB ratio*/Critical Wavelength* | 0.75/384 nm |

Technical Data

| | |
|---|---|
| pH value | 7.00 |
| Appearance | white lotion |
| Viscosity (Brookfield DVIII + LV4/80 rpm) | 3000 mPas |
| UVA/UVB ratio*/Critical Wavelength* | 0.75/384 nm |

Example 3

Sun Protection Cream

In this sun protection cream, in order to obtain a wide-scale antimicrobial effect, there was used a compound mixture (HMR-5) extracted from stem knotwood chips from *picea abies* in pentylene glycol. HMR-5 was an unpurified raw extract and contained 10 wt % of the compound mixture and 90 wt % of pentylene glycol. At the same time, HMR-5 also served as a trapper of free radicals induced by possible sunlight or by particles released from an organic UV protection agent, thus increasing the in vivo protective factor on the skin. The extraxt also stabilizes vitamine C. The sun protection cream contained UV protection agents that protect the skin both against UVA and UVB rays (Granlux GA12-45 and an organic protection agent).

| Part 1 | |
|---|---|
| Granlux ® GA12-45: (Granula Ltd) | 28% |
| Concentrate containing inorganic UV protection agents (TiO₂ and ZnO) protected by aluminum oxide, dispersed in dimethicone and surface active dispersing agent | |
| Glycerine | 4% |

| Part 2 | |
|---|---|
| alpha-Bisapolol | 1.5% |
| *Bytospermum parkii* Fruit | 1.5% |
| Cetiol CC | 0.1% |
| Oxynex K Fluido | 0.1% |
| Alkyl benzoate | 4% |

| Part 3 | |
|---|---|
| Water | 23.5% |
| *Aloe barnadensis* | 1% |
| Multivitamin product | 0.3% |
| Dinatrium EDTA | 0.1% |

| Part 4 | |
|---|---|
| Cyclomethicone | 1.5% |
| Ethylhexyl methoxycinnamate | 5% |
| Organic UV protection agent | 2% |
| Homosalate | 5% |

| Part 5 | |
|---|---|
| Ethylhexyl glycerine | 0.5% |
| HMR-5 (intermediate product of example 1) | 3% |

Parts 1-5 were mixed as a sun protection cream by conventional methods.

Example 4

Cleaning Cloth Containing Antimicrobial Compound Mixture According to the Invention This can be manufactured as is described in the U.S. Pat. No. 6,287,582. The cloth contains a water-insoluble carrier and a cosmetic composition impregnated in the carrier, including a compound mixture according to the invention, pH regulator such as alpha- or beta-hydroxycarboxylic acid, silicone microemulsion and surface active agent. The pH of the cosmetic composition in water is no more than 6. The microemulsion is for example a dimethiconol microemulsion.

In the Table below, there are given two exemplary compositions to be impregnated in a cleaning cloth, containing an extracted wood knot mixture according to the invention.

| Ingredient | Acceptable range (Percent by weight) |
|---|---|
| Dual chain quaternary (N-alkyl dimethyl Ethylbenzyl chloride or N-alkyldiemethyl Ethylbenzyl ammonium chloride) | 0.0-2.0 |
| Ortho phenyl phenol | 0.0025-2.0 |
| Paratertiary amyl phenol | 0.0025-2.0 |
| Extracted knot mixture in alcohol (Granula Ltd) | 1.0-40.0 |
| Tergitol 15-S-5 | 0.5-2.0 |
| Citric acid | 0.1-2.0 |
| Emollient | 0.1-3.0 |
| Water | Up to 100 |

| Ingredient | Specific composition formulation (Percent by weight) |
|---|---|
| Dual chain quaternary (N-alkyldimethylethylbenzyl chloride or N-alkyldimethylethylbenzyl ammonium chloride) | 0-0.25 |
| Ortho phenyl phenol | 0.0125 |
| Paratertiary amyl phenol | 0.0025 |
| Extracted knot mixture in alcohol (Granula Ltd) | 0.01-40.0 |
| Tergitol 15-S-5 | 0.5 |
| Citric acid | 0.05 |
| Aloe vera gel | 1.0 |
| Water | Up to 100 |

Example 5

This formulation is good for wound healing and skin remedy

Aftershave Gel without Alcohol

| Trade name/INCI | p-% |
|---|---|
| A | |
| Carbopol 940/Carbomer | 0.30 |
| Water dem. Aqua dem. | 40.00 |
| B | |
| Cremophor CO 40/PEG-40/Hydrogenated castor oil | 3.00 |
| Perfume | q.s. |
| Menthol | 0.10 |
| D-Panthenol 50 P/Panthenol, | 0.10 |
| 10% Extracted Spruce and/or Pine knot mixture in propylene glycol | 4.00* |
| Triethanolamine | 0.40 |
| Water Aqua dem. | up to 100% |
| Production | |

Let phase A swell. Phase B is dissolved and mixed in phase A.

Viscosity: roughly 4 000 mPa s (Brookfield RVT), pH value roughly 7.

*a compound mixture of phenolic compounds obtained from knotty stemwood chips in propylene glycol extraction, contg. 10 wt % of the compound mixture and 90 wt % of propylene glycol.

Example 6

Rehydrating Aftersun Mist

In the production of this aqueous mist-like composition, there was used a water component, emulgator (Luviquat®Mono CP) and PEG-40, a surface active silicone-based agent (Dow Corning 190 Surfactant), a moisturizer (D-panthenol), and a moisturizing agent Prodew® 200. The growth of micro-organisms was inhibited by a compound mixture of phenolic compounds, obtained in pentylene glycol extraction from chips contained in knotty spruce stemwood in mixture, contg. 10 wt % of the compound mixture and 90 wt % of propylene glycol. This raw extract was used unrefined in the production of mist.

| Trade name/INCI | wt % |
|---|---|
| A | |
| Deionized water | 89.10 |
| Luviquat ® Mono CP/Hydroxyethyl cetyl dimonium phosphate (1) | 2.00 |
| D-Panthenol (1) | 0.50 |
| 10% Extracted knot mixture in pentylene glycol (5)* | 5.50 |
| Dow Corning 190 Surfactant/Dimethicone polyol (2) | 0.50 |
| Prodew ® 200/Sodium lactate & Sodium PCA & Sorbitol & Hydrolyzed Collagen & Proline (3) | 2.00 |
| B | |
| Cremophor ® RH 40/PEG-40, Hydrated castor oil (1) | 0.30 |
| Perfume | 0.10 |
| Production | |

Combine ingredients of phase A and stir until solution is clear.

Combine ingredients of phase B. Melt hydrated castor oil and stir with perfume.

Combine phase B with A and stir until mixture is clear.

pH of the end product is 6.

*polyphenolic mixture obtained from wood chips contained in knotty stemwood in pentylene glycol extraction, contg. 10 wt % of the extract mixture and 90 wt % of propylene glycol.

Suppliers
(1) BASF
(2) Dow Corning
(3) Ajinomoto
(4) Nipa
(5) Granula Ltd

Example 7

Body Milk

The body milk according to Example 6 is an aqueous emulsion, in the manufacturing of which there are used emulsifying agents (Cremophor), auxiliary agent (glyceryl monostearate) as well as water and oil components, viscosity regulator (cetyl stearyl alcohol), emollients (Luvitol EHO) and conditioner (Luviquat PQ 11). The growth of micro-organisms was inhibited by a compound mixture of phenolic compounds obtained from knotty spruce stemwood in butylene glycol extraction, which mixture contained phenolic compounds 10 wt %, and which raw extract was used unrefined for the production of body milk.

| Trade name/INCI | wt % |
|---|---|
| A | |
| Cremophor A 6/Ceteareth-6, Stearyl alcohol | 1.00 |
| Cremophor A 25/Ceteareth-25 | 1.00 |
| Glyceryl monostearate | 2.00 |
| Cetyl stearyl alcohol | 2.00 |
| Paraffin oil/Mineral oil | 3.00 |
| Luvitol EHO/Cetyl stearyl octanoate | 5.00 |
| B | |
| 10 wt % extracted knot mixture in butylene glycol* | 5.00 |
| Luviquat PQ 11 (1) Polyquaternium-11 | 4.00 |
| Water | 77.00 |
| C | |
| Perfume | q.s. |
| Production | |

Mix phases A and B separately at roughly 80° C. Mix phase B to phase A whilst homogenizing, and continue homogenizing for a while. Cool roughly at 80° C., add phase C and homogenize again.

Viscosity: roughly 3000 mPas pH: roughly 6

*polyphenolic mixture obtained from wood chips contained in knotty stemwood in butylene glycol extraction, contg. 10 wt % extract mixture and 90 wt % butylene glycol.

Example 8

Concenrated Powder

| Trade name/INCI | wt % |
|---|---|
| A | |
| Talcum | 72.00 |
| Magnesium stearate | 10.00 |
| Calcium carbonate | 2.00 |
| Sicovit White E 171/C,I. 77891/Titanium oxide | 9.00 |
| Sicovit Brown 70 E 172/Ferric oxides | 1.00 |
| Powdered knot mixture | 5.00 |
| B | |
| Paraffin oil/Mineral oil | 0.50 |
| Vaseline/Petrolatum | 0.50 |
| Production | |
| Mix ingredients of phase A and homogenize. Stir phase B to phase A and mix again. | |

Example 9

Cell-protective Composition

| Trade name, compound/INCI | wt % |
|---|---|
| A | |
| RonaCare ™ Ectoin (1) | 1.00 |
| 10% Extracted Spruce and/or Pine knot mixture in Pentylene Glycol (5) | 3.00 |
| Water, mineralized | up to 100% |
| B | |
| Sisterna SP30-C (2)/saccharose distearate | 2.70 |
| Sisterna SP70-C (2)/saccharose stearate | 0.90 |
| Cetiol OE (3)/dicapryl ether | 5.00 |
| Miglyol 812 (1)/kaprylic/kapric triglyceride | 2.00 |
| Isopropyl palmitate (3)/isopropyl palmitate | 2 |
| Cegesoft C 24 (3)/ethylhexyl palmitate | 7.00 |
| Carbopol ETD 2001 (4)/carbomer | 0.20 |
| C | |
| Sodium hydroxide, 10% solution (1)/sodium hydroxide q.s. | |
| Production | |
| Heat phase A to 75° C., disperse phase B and heat to 75° C., add phase B to phase A, homogenize, adjust pH with sodium hydroxide, cool to room temperature by stirring simultaneously. | |
| Note | |
| pH (22° C.): 6.50 | |
| Viscosity (21° C.): 109 000 mPa · s (Brookfield RVT, spindle C, 5 rpm, Helipath) | |
| Suppliers | |
| (1) Merck KGaA/Rona ® | |
| (2) Sisterna C.V./Dai-Ichi | |
| (3) Cognis GmbH | |
| (4) B F Goodrich GmbH | |
| (5) Granula Ltd | |

Example 10

Night Care Cream

For producing this cream-like composition, there was used a water component, emulsifying agents (PEG-7), emollients (Luvitol EHO), wax components and fungicidal and moisturizing agents (jojoba oil). The growth of antimicrobial agents was prevented by jojoba oil and by a compound mixture of phenolic compounds, obtained from knotty spruce stemwood in glycerine extraction, which mixture contained phenolic compounds 10 wt %, and which raw extract was used unrefined for producing the cream.

| Trade name/INCI | wt % |
|---|---|
| A | |
| Cremophor WO 7/PEG-7 Hydrated castor oil | 6.00 |
| Luvitol EHO/Cetearyl octanoate | 5.00 |
| Permulgin 3220/Microcrystalline wax | 2.00 |
| Beeswax | 0.50 |
| Cetiol SB 45/Shea Butter (*Butyrospermum parkii*) | 0.50 |
| Jojoba oil/Jojoba (*Buxus chinensis*) oil | 2.00 |
| Paraffin oil/Mineral oil | 10.00 |
| B | |
| 10% Extracted knot mixture in glycerin | 5.00 |
| Water | 67.00 |
| C | |
| Sodium ascorbyl sorbate | 2.00 |
| Perfume | q.s. |
| Production | |
| Mix phases A and B separately to roughly 80° C. Stir phase B to phase A whilst homogenizing, continue homogenizing for a while. Cool to roughly 40° C., add C and homogenize again. | |

Example 11

Night Care Cream

The night care cream according to example 10 was almost identical to night care cream of example 9, but instead of sodium ascorbyl sorbate of example 9, sodium ascorbyl phosphate was used in example 10 as an antioxidant agent. The wood knot extract stabilizes the vitamine and provides preservation and improves antioxidant action.

| Trade name/INCI | wt % |
|---|---|
| A | |
| Cremophor WO 7/PEG-7 Hydrogenated Castor Oil | 6.00 |
| Luvitol EHO/Cetearyl Octanoate | 5.00 |
| Permulgin 3220/Microcrystalline Wax | 2.00 |
| Beeswax | 0.50 |
| Cetiol SB 45/Shea Butter (*Butyrospermum parkii*) | 0.50 |
| Jojoba Oil/Jojoba (*Buxus chinensis*) Oil | 2.00 |
| Paraffin Oil/Mineral Oil | 10.00 |
| B | |
| 10% Extracted Spruce and/or Pine knot mixture in glycerine | 5.00 |
| Water | 67.00 |
| C | |
| Sodium Ascorbyl Phosphate | 2.00 |
| Perfume | q.s. |
| Production | |
| Heat phases A and B separately to about 80° C. Stir phase B into phase A whilst homogenizing and continue homogenizing for a while. Cool to about 40° C., add phase C and homogenize again. | |

Example 12

Softcream with Vitamine E

For making softcream of example 11, there were used several emollients, oil and water components, preservatives, adjuvants and other additives including vitamins for antioxidant purposes. Growth of micro-organisms (bacteria, fungi, yeast) was inhibited by a compound mixture of 10 wt % raw extract (from spruce and/or pine) including phenolic compounds in glycerin (10 wt % of mixture of compounds and 90 wt % of glycerin). This glycerin containing raw extract was used without further purification.

| Trade name/INCI | wt % |
|---|---|
| A | |
| Cremophor GO 32/Polyglyceryl-3 Dioleate | 0.75 |
| Luvitol EHO/Cetearyl Octanoate | 7.50 |
| Finsolv TN/Alkyl Benzoate | 5.00 |
| Miglyol 812/Caprylic/Capric Triglyceride | 4.00 |
| Abil EM 90/Cetyl Diethicone Copolyol | 2.25 |
| Abil 350/Dimethicone | 1.50 |
| Ascorbyl Palmitate, Citric Acid, Glyceryl Stearate, Propylene Glycol | 0.20 |
| B | |
| 10% Extracted Spruce and/or Pine knot mixture in Glycerin | 0.75 |
| Sodium Hydroxide | 0.25 |
| D-Panthenol USP/Panthenol | 1.50 |
| Sodium Chloride | 1.50 |
| EDTA | 0.1 |
| Preservative | q.s. |
| Water | 69.80 |
| C | |
| (−)-Alpha-Bisabolol nat./Bisabolol | 0.10 |
| Vitamin A Palmitate 1 Mio./Retinyl Palmitate | 0.10 |
| Vitamin E Acetate/Tocopheryl Acetate | 5.00 |
| Perfume | q.s. |
| Production | |

Heat phases A and B separately to about 80° C. Stir phase B into phase A whilst homogenizing. Cool to about 40° C., add phase C and homogenize again.
Viscosity: approx. 18 000 mPas

Example 13

Multi-Vitamin Cream, Typ W/O Formula

For manufacturing this W/O-type cream composition, water and oil were used as carrier agents, as an adjuvant emulgators (PEG-7, PEG-45, Claytone XL), and as an additive moisturizer (Jojoba oil,) perfume and vitamins (sodium ascorbyl phosphate and retinol). Growth of micro-organisms (bacteria, fungi, yeast) was inhibited by a compound mixture of 10 wt % extracted mixture (spruce) containing phenolic compounds extracted from spruce knots into butylene glycol (10 wt % of mixture of phenolic compounds and 90 wt % of butylene glycol). This raw extract was used without further purification.

| Trade name/INCI | wt % |
|---|---|
| A | |
| Cremophor WO 7/PEG-7 Hydrogenated Castor Oil | 6.00 |
| Paraffin Oil/Mineral Oil | 10.00 |
| Vaseline/Petrolatum | 3.00 |
| Miglyol 812/Caprylic/Capric Triglyceride | 5.00 |
| Elfacos ST 9/PEG-45/Dodecyl Glycol Copolymer | 2.00 |
| Jojoba Oil/Jojoba (*Buxus Chinensis*) Oil | 5.00 |
| Claytone XL/Quaternium-18 Bentonite | 1.00 |

| Trade name/INCI | wt % |
|---|---|
| B | |
| 10% Wood Knot Extract in Butylene Glycol | 4.00 |
| EDTA | 0.10 |
| Water | 61.90 |
| C | |
| Sodium Ascorbyl Phosphate | 1.00 |
| Retinol | 1.00 |
| Perfume | q.s. |
| Production | |

Heat phases A and B separately to about 80° C. Stir phase B into phase A whilst homogenizing and continue homogenizing for a while. Cool to about 40° C., add phase C and homogenize again.
Viscosity: approx. 14 000 mPa s (Haake Viscotester VT-02).

Example 14

GAI-45 TS High SPF Cream

This composition was made of water phase, semi-composition of GranLux® GAI-45 TS which is an W/O-emulsion including UV-protective agents in a silicon emulsifier system and 10 wt % mixture of phenolic compounds originating to spruce knots and extracted into pentylene glycol (10 wt % of mixture of phenolic lignan compounds and 90 wt % of pentylene glycol). The end composition included also emollient and dispersive oil (isononyl isononanoate) and perfume.

| Trade name/INCI | Amount (%) | Manufacturer |
|---|---|---|
| A | | |
| GranLux ® GAI-45 TS | 25.0 | Granula Ltd |
| 10% extracted mixture in pentylene Glycol | 3.0 | Granula Ltd |
| B | | |
| Water | 10.0 | |
| C | | |
| Isononyl Isononanoate | 22.0 | Seppic |
| D | | |
| Water | 39.0 | |
| Perfume | q.s. | |

1) Mix A at room temperature.
2) Prepare B and add it to A. Mix ca 3-5 min until all water has been taken up. The water will go in by diffusion, hydrate the polar parts and form the liquid crystalline phase. The polar phase and the hydrophobic phase seem initially to be totally separated but the water phase will be taken up by time and mixing.
3) Add to C to A + B while mixing. Viscosity goes down.
4) Add D to C + A + B slowly (during ca 5 minutes) while processing well (Ystral speed 3-5) for totally 15 minutes.
SPF: well over 30 (SPF in vitro 49 +/− 3)
UVA: fulfills "Australian Standard"

Example 15

Fluid Foundation using Granlux™ Melanin Mimic™ TB Concentrate

For making this composition there was used a semi-composition Granlux™ Melanin Mimic™ which is a formula imitating the UV-protection of natural melanin. Growth of micro-organisms (bacteria, fungi, yeast) was inhibited by a compound mixture of 10 wt % mixture of phenolic compounds extracted from spruce knots in pentylene glycol (10 wt % of mixture of phenolic compounds and 90 wt % of pentylene glycol). This raw extract was used without further purification. Also betulonic acid originating to birch bark was used as an antimicrobial agent.

| Trade name/INCI | Amount (wt %) | Manufacturer |
|---|---|---|
| A | | |
| Magnesium aluminum silicate (Veegum K) | 0.70 | Vanderbilt |
| Xanthan gum (Rodicare) | 0.30 | Rhône Poulenc |
| 10% extracted polyphenolic mixture in pentylene glycol | 6.00 | Granula Ltd |
| Glycerine | 4.00 | |
| Deionized water | q.s. | |
| Wet the Xanthan gum in water + glycerine + 10 wt % polyphenolic mixture extracted from spruce knots into pentylene + 10 wt % Betulonic acid in propylene glycol. Homogenize with turboemulsifier and add Magnesium aluminum silicate while mixing, heat to 75° C. | | |
| B | | |
| Granlux ™ Melanin Mimic ™ | 27.50 | Granula Ltd |
| *Limnanthes alba*; *Butyrospermum parkii* (Fancol VB) | 3.50 | The Fanning Co |
| Glyceryl stearate (Tegin M) | 0.80 | Th. Goldschmidt |
| Isopropyl myristate | 4.00 | |
| Isohexadecane (Arlamol HD) | 10.00 | ICI |
| Stearic acid | 2.00 | |
| Dimethicone (Dow Corning 200 Fluid 100 cs) | 1.00 | Dow Corning |
| Melt Phase B at 65° C., slowly homogenizing for ca 5 min, heat to 75° C. | | |
| B1 | | |
| Talcum | 1.00 | |
| Add Phase A to Phases B while homogenizing. As emulsion is formed, add Phases B1 and C slowly while continuing homogenizing. | | |
| C | | |
| Triethanolamine | 1.50 | |
| D | | |
| PPG 25 Laureth 25 (ADF Oleile) | 0.20 | Vevy |
| At 40° C. add Phase D while homogenizing. Cool to room temperature while mixing. | | |
| Characteristics: | | |
| pH: ca 7 | | |
| Viscosity: 6.000 | | |
| SPF: 21-24 | | |

Example 16

This product is good for protecting and curing the skin against UV and UV induced damage. It also gives some colour.
Soft Coloured Cream (SCC/EM/98)

| INCI(Trade name) | Amount (%) | Manufacturer |
|---|---|---|
| A | | |
| Magnesium aluminum silicate (Veegum K) | 0.50 | Vanderbilt |
| Xanthan gum (Rodicare) | 0.50 | Rhône Poulenc |
| Propylene glycol | 6.00 | |
| 10% Betulonic acid in Glycerine | 4.00 | Granula Ltd |
| Deionized water | up to 100% | |
| Wet the Xanthan gum in water + betulonic acid in glycerine + propylene glycol. Homogenize with turboemulsifier and add Magnesium aluminum silicate while mixing, heat to 75° C. | | |
| B | | |
| Granlux ® EM-50 | 10.00 | Granula Ltd |
| *Limnanthes alba*; *Butyrospermum parkii* (Fancol VB) | 3.50 | The Fanning Co |
| Glyceryl stearate (Tegin M) | 0.80 | Th. Goldschmidt |
| Isopropyl myristate | 4.00 | |
| Isohexadecane (Arlamol HD) | 10.00 | ICI |
| Polydecene (Nexbase 2004 FG) | 4.00 | Fortum |
| Polyhydroxystearic acid (Arlacel P100) | 0.50 | ICI |
| Melt Phase B at 65° C., add Phase B1 slowly homogenizing for ca 5 min, heat to 75° C. | | |
| B1 | | |
| CI 77492 (Ariabel yellow) | 1.40 | Warner&Jenkinson |
| CI 77491 + CI 77492 (Ariabel sienna) | 0.30 | Warner&Jenkinson |
| CI 77491 + CI 77492 CI 77499 (Ariabel umber) | 0.30 | Warner&Jenkinson |
| CI 77891 (Titanium dioxide) (Kemira AFDC) | 6.00 | Kemira |
| Add Phase A to Phases B + B1 while homogenizing. As emulsion is formed, add Phase C while continuing homogenizing. | | |
| C | | |
| Talcum | 1.00 | |
| Aluminum starch octenylsuccinate (Dry-Flo PC) | 3.00 | National Starch |
| D | | |
| PPG 25 Laureth 25 (ADF Oleile) | 0.20 | Vevy |
| Propylene glycol; Diazolidinyl urea; Methyl paraben; Propylparaben (Germaben II E) | 1.00 | ISP |
| At 40° C. add Phase D whilst homogenizing. Cool to room temperature while mixing. Note: During the preparation the phase inversion temperature is clearly noticeable (PIT ca 40°) since the W/O system previously formed breaks into two phases: one liquid and one creamy. While continuing homogenization, the final emulsion (O/W) is easily obtained. The low value of PIT is not related to unstable behavior, in fact the formulation is still stable after 4 months at 42° C. | | |
| Characteristics: | | |
| pH: ca 7 | | |
| Viscosity: 180.000 mPa s RVT Brookfield (5 rpm, 298 K, Helipath Stand T-D | | |
| SPF: 21-23 in vitro, UVA/UVB = 0.77 | | |

Example 17

A stick with UV-protection of SPF 15 was made from semi-composition of Granlux CCA-50, which includes mainly physical filter for UV-protection, beeswax and carnauba wax. Large-scale protection against micro-organisms (bacteria, yeast, fungi) is achieved by a powdered compound mixture originating to pulverized spruce and/or pine knots.

UV-Protective Stick, SPF 15

| | | |
|---|---|---|
| Hydrogenated Vegetable Oil (Cremeol HF-52) | 15.0 | Aarhus Olie |
| Vegetable Oil (Cremeol PS-6) | 68.0 | Aarhus Olie |
| Candelilla wax | 6.0 | |
| Powdered knot mixture of spruce and/or pine wood knot | 1.0 | Oy Granula Ab, Ltd |
| Granlux CCA-50 | 10.0 | Oy Granula Ab, Ltd |

Heat ingredients to 75-80° C. Mix until uniform. Cool to 50° C. Pour into moulds.

Characteristics:

SPF: 13-15 in vitro
UVA/UVB ratio 0.56

Example 18

UV-protective stick, SPF 30

A stick with UV-protection of SPF 30 was made from semi-composition of Granlux CCA-50, which includes mainly physical filter for UV protection, beeswax and carnauba wax. Large-scale protection against micro-organisms (bacteria, yeast, fungi) is achieved by a powdered compound mixture originating to pulverized spruce and /or pine knots.

| Trade name/INCI | wt % | |
|---|---|---|
| Beeswax (Cera alba) | 12.0 | |
| Caprylic Capric Triglycerides | 12.5 | |
| Macadamia nut oil | 9.5 | |
| Cetearyl alcohol | 7.5 | Henkel |
| Petrolatum | 36.5 | |
| Granlux CCA-50 | 20.0 | Oy Granula Ab, Ltd |
| Powdered knot mixture of spruce and/or pine wood knot | 2.0 | Oy Granula Ab, Ltd |

Heat ingredients to 75-80° C. Mix until uniform. Pour into molds.

Characteristics:

SPF: 28-30 in vitro

Example 19

Sun Protection Gel

| Trade name/INCI | wt % |
|---|---|
| A | |
| Uvinul MC 80/Octyl Methoxycinnamate | 8.00 |
| Uvinul N 539 T/Octocrylene | 5.00 |
| Uvinul M 40/Benzophenone-3 | 2.00 |
| Parsol 1789/Butyl Methoxydibenzoylmethane | 0.80 |
| Vitamin E Acetate/Tocopheryl Acetate | 2.00 |
| Cremophor RH 410/PEG-40 Hydrogenated Castor Oil | 1.00 |
| Perfume | q.s. |
| B | |
| Pemulen TR-1/Acrylates/C10-30 Alkyl Acrylate Crosspolymer | 0.30 |
| Carbopol 940/Carbomer | 0.20 |
| 10% Extracted Spruce and/or Pine knot mixture in Dioctyl Glycol | 5.00 (Granula Ltd) |
| Edeta BD/EDTA | 0.20 |
| Water | 75.30 |

| Trade name/INCI | wt % |
|---|---|
| C | |
| Sodium Hydroxide | 0.20 |

Production

Dissolve phase A. Stir phase B into phase A whilst homogenizing, then neutralize with phase C and homogenize again.
Viscosity: approx. 5 500 mPa s (Haake Viscotester VT-02)
pH-value: approx. 9.1.

Example 20

Sunscreen Foam

Mixture of phenols was extracted from particles of knotwood of spruce and/or pine into pentylene glycol. The amount of mixture of phenolic compounds in final composition was 0.05 wt %. The Sunscreen Foam also contains various organic compounds (Octyl Methoxycinnamate, Octyl Triazone and 4-Methylbenzylidene Camphor) having protective properties against UV-radiation.

| Trade name/INCI | wt % |
|---|---|
| A | |
| Cremophor A 25/Ceteareth-25 | 5.00 |
| Palmitic Acid | 2.00 |
| Finsolv TN/Alkyl Benzoate | 5.00 |
| Witconol APM/PPG-3 Myristyl Ether | 5.00 |
| Uvinul MC 80/Octyl Methoxycinnamate | 6.00 |
| Uvinul T 150/Octyl Triazone | 0.50 |
| Uvinul MBC 95/4-Methylbenzylidene Camphor | 1.00 |
| B | |
| 10% Extracted Spruce and/or Pine knot mixture in Pentylene Glycol | 5.00 |
| Water | 70.30 |
| C | |
| Triethanolamine | 0.20 |
| D | |
| Perfume | q.s. |

Production

Heat phases A and B separately to about 80° C. Stir phase B into phase A whilst homogenizing. Stir in phase C and rehomogenize. Cool to about 40° C., add phase D and homogenize again.
Filling: 90% active ingredient
10% propane/butane 3.5 bar (20° C.).

Example 21

Anti-scurf Compositions

Compound mixtures according to the invention inhibit microbial growth on a wide scale, so that they can be used for replacing several specific preservatives in cosmetic compositions, i.e. specifically agents designed individually against Gram-negative and Gram-positive bacteria, fungi and yeast. Moreover, the cytotoxicity of said compound mixtures is low, and the compounds contained therein do not penetrate the skin, wherefore their skin irritation low, as opposite to certain conventionally used agents inhibiting the growth of antimicrobial agents on a wide scale, such as phenoxyethanol.

The compound mixtures according to the invention are effective against the yeast Malassezia furfur, wherefore they can be used as both wide-scale preservatives and also for inhibiting the action of the scurf forming yeast Malassezia furfur. Generally with scurf shampoo compositions it is necessary to separately add both preservatives, such as wide-scale bacteriostat phenoxyethanol, and further also separately an agent inhibiting the growth of scurf forming yeast. Owing to their toxicity and skin penetration, generally used wide-scale preservatives cannot be used in quantities sufficiently large in order to ensure the inhibition of the growth of the scurf-forming yeast; whereas the compound mixtures according to the invention have a low skin penetration, so that they can be used in relatively large quantities in cosmetic compositions.

Example 22

Oil Shampoo

| Ingredient | Wt %" |
| --- | --- |
| Sodium lauryl sulfate (Texapon N25) | 50 |
| PPG-5 Laureth-5 (Aetoxal B) | 20 |
| Cocoamide DEA (Comperlan KD) | 3 |
| GranLux AOX-G3 Eco | 5 |
| (10 wt % Spruce knot extract in propylen-1.3-diol) | |
| Aqua and perfume | 22 |

Oil shampoo has a clear continuous water phase with 0.5 wt % mixture of compounds originating to spruce knots, extracted with alcohol (propyle-1.3-diol). Spruce knot extract gives anti-scurf properties (against $M. furfur$) to oil shampoo. The amount of water can be reduced substantially for example to 5-20% if this oil shampoo is intended for large-scale consumers.

Example 23

Combined Hair Conditioner and Shampoo

| Ingredient | Wt %" |
| --- | --- |
| Coco-Betaine (Dehyton AB 30) | 20% |
| PEG-5 Cocoamide (Emulgin C4) | 20% |
| Cocoamid MEA (Comperlan KM) | 4% |
| Laurtrimonium Chloride (Dehyquat LT) | 4% |
| Granlux AOX-GL (10% Spruce knot extract in glycerine) | 4% |
| Aqua and perfume | 48% |

Combined hair conditioner and shampoo has also a clear continuous water phase as a carrier agent with 0.4 wt % mixture of compounds originating to spruce knots, extracted with alcohol (glycerine). Spruce knot extract gives anti-scurf properties (against $M. furfur$) to hair conditioner and shampoo. The amount of water can be reduced substantially for example to 5-20% if this hair conditioner and shampoo is intended for large-scale consumers.

Example 24

Vitaminized Protein Shampoo

| Ingredient | Wt %" |
| --- | --- |
| Polysorbate 20 (Tween 20) | 10 |
| Polysorbate 80 (Tween 80) | 5 |
| PEG-54 Hydrogenated Castor oil(Arlatone 289) | 10 |
| PPG-15 Stearyl Ether (Arlamol E) | 2 |
| Cocoamid DEA | 5 |
| Cocoamidopropyl Betain (Tegobetain L7) | 3 |
| Hydrolized collagen (Nutrilan L) | 5 |
| Vitamin F (Novarom) | 2.5 |
| Granlux AOX (10% Spruce knot extract in butylene glycol) | 5 |
| Aqua and perfume | 27.5 |

Vitaminized protein shampoo is a turbid O/W emulsion/dispersion with 0.5 wt % mixture of compounds originating to spruce knots, extracted with alcohol (butylene glycol). Spruce knot extract gives anti-scurf properties (against $M. furfur$) to hair conditioner and shampoo. The amount of water can be reduced substantially for example to 5-20% if this vitaminized shampoo is intended for large-scale consumers. This composition also contains an amphoteric surfactant (cocoamidopropyl betain), foaming agent (Cocoamid DEA), and ionic surfactants (polysorbates).

Example 26

Animal Feed

Into soybean feed, there was added by spraying a raw extract, with an alcohol content of 90-95 wt %, and compound mixture 5-10 wt %. The compound mixture was obtained by extracting either a lignan mixture obtained from Norway spruce knotwood by extraction with alcohol (extracted knot mixture from spruce), or mixed extract obtained from Norway spruce and pine knotwood by extraction with alcohol, which mixed extract included a compound mixture containing lignans and stilbenes.

Example 27

A feed composition for domestic mammals comprising spruce knot extact or pine knot extract or any mixture of them at a concentration of 0.1-15 wt % and at least one component selected from a group consisting of meat and bone meal, blood meal, poultry byproduct meal, tallow, wheat middlings, roughage products, oat groats, alfalfa meal, bakery by-products, brewers dried grains, distillers dried grains and solubles, citrus pulp, beet pulp, corn gluten feed, corn gluten meal, cottonseed meal, fish meal, hominy feed, kelp meal, linseed meal, sunflower meal, canola and rapeseed meal, and rice bran.

Example 28

This is a example of a semi finished UV-protection product containing wood knot extract.

Wood knot extract, such as spruce knot extact or pine knot extract or any mixture of them, at a concentration of 0.1-15 wt % mixed in any UV-protection concentrate, such as GranLux-products (produced by Granula Ltd).

| | |
|---|---|
| Wood knot extract | 2-10% |
| GranLux concentrate | 98-90% |

In the examples 3-24, the term extracted wood knot mixture or extracted knot mixture or wood knot extract refers to the extracted solution containing (poly)phenolic compounds including compound mixture according to the invention, which mixture is obtained by extracting stem knotwood chips in alcohol and/or glycol. A powdered wood knot mixture of powdered knot mixture or wood knot powder in turn refers to a corresponding pulverized mixture, which is obtained by pulverizing stem knotwood chips. Mixed extracts of pine and spruce contained 1 part by volume of extracted knot mixture from pine, and 4 parts by volume of extracted knot mixture from spruce. Powdered knot mixtures originating from spruce and pine contained 1 part by weight pulverized pine and 3 parts by weight pulverized spruce.

As presented in example 6 the compound mixtures according to invention can also be used as a wound healing agent in various cosmetic compositions.

In examples 1-24 powdered or extracted mixed wood knot mixtures originating from spruce knotwood and pine knotwood the composition of compound mixtures were blends of phenolic compounds indicated in table 1 (pine) and table 2A (spruce). Powdered or extracted wood knot mixtures originating from spruce knotwood the composition of phenolic compound mixture was similar indicated in table 2A. However it should be understood that instead of pine and spruce species whose composition of phenolic compound mixture is indicated in table 1 and 2A it can also other pine and spruce species be used, for example those whose composition of phenolic compound mixture is given in table 3B

The invention claimed is:

1. A composition comprising:
   (a) a compound mixture obtained from pulverized and/or extracted wood material being present at 0.1-5 wt % of the composition,
   (b) an antimicrobial agent ethylhexyl glyceryl, and
   (c) a carrier agent,
   wherein said compound mixture of part (a) comprises:
   (i) lignans present 50-99 wt % of the compound mixture, said lignans comprising at least one of: 7-hydroxymatairesinol, isohydroxymatairesinol, cyclolariciresinol, secoisolariciresinol, anhydrosecoisolariciresinol, conidendrin, conidendric acid, alpha-conidendrin and alpha-conidendric acid,
   (ii) stilbenes present at 0.1-70 wt % of the mixture, and
   (iii) oligomers of lignans, stilbenes, juvabiones or flavonoids present at 1-31 wt % of the compound mixture.

2. The composition of claim 1, wherein said carrier agent is suitable for use in cosmetics or food.

3. The composition of claim 1, further comprising antioxidative agents selected from the group consisting of beta carotenes, selenium, glutamine, ubiquinone, glycolic acid, growth hormones and kinetin.

4. The composition of claim 1, wherein said carrier is a homogeneous solution, a colloid, an aerosol, paste, mist, foam, suspension, dispersion, gel, solid foam, solid matter, emulsion, microemulsion, nanoemulsion or a heterogeneous mixture.

5. The composition of claim 1, further comprising at least one surface active agent, dispersing agent, perfume, viscosity regulator or a moisturizer.

6. The composition of claim 5, comprising at least one surface active agent, wherein said surface active agent one of cetearyl pyridium chloride, bentsalkonium chloride, ionogenic agent, cetearyl glycoside, lower alcoxilated glycosides, a micelle-forming agent, or lecithin.

7. The composition of claim 1, further comprising lignans obtained from flaxseeds and UV protective agents.

8. The composition of claim 1, wherein said composition is a hair care product capable of inhibiting the growth of scurf-causing yeast, *Malassezia furfur*, said composition comprising an aqueous carrier agent.

9. The composition of claim 1, wherein said composition is a dermatological composition.

10. The composition of claim 1, wherein said composition is a sun protective composition in which said carrier agent is a cream.

11. The composition of claim 1, further comprising at least one of betulin, betulonic acid, betulinic acid or betuloinic acid.

12. The composition of claim 1, wherein the compound mixture comprises:
   (i) 7-hydroxymatairesinol, secoisolariciresinol or a combination thereof, 50-99.9 wt %;
   (ii) pinosylvin, 0.1-20 wt %;
   (iii) oligomers of lignans, stilbenes, juvabiones or flavonoids, 5-8 wt %;
   (iv) conidendrin, 3-6 wt %;
   (v) lariciresonil 4-7 wt %; and
   (vi) liovile 2-5 wt %.

* * * * *